(12) United States Patent
Weaver et al.

(10) Patent No.: US 7,268,164 B2
(45) Date of Patent: Sep. 11, 2007

(54) ANTI-EPILEPTOGENIC AGENTS

(75) Inventors: Donald E. Weaver, Kingston (CA); Paul H. Milne, Ottawa (CA); Christopher Y. K. Tan, Kingston (CA); John R. Carran, Kingston (CA)

(73) Assignee: Queens University at Kingston, Kingston, Ontario (CA)

( * ) Notice: Subject to any disclaimer, the term of this patent is extended or adjusted under 35 U.S.C. 154(b) by 555 days.

(21) Appl. No.: 09/932,677

(22) Filed: Aug. 16, 2001

(65) Prior Publication Data

US 2003/0229144 A1 Dec. 11, 2003

Related U.S. Application Data

(62) Division of application No. 09/041,371, filed on Mar. 11, 1998, now Pat. No. 6,306,909.

(60) Provisional application No. 60/073,536, filed on Feb. 3, 1998, provisional application No. 60/041,140, filed on Mar. 12, 1997.

(51) Int. Cl.
*A61K 31/195* (2006.01)
(52) U.S. Cl. ...................... 514/562; 562/576
(58) Field of Classification Search ............... 514/567; 562/576
See application file for complete search history.

(56) References Cited

U.S. PATENT DOCUMENTS

| | | | |
|---|---|---|---|
| 2,461,842 A | 2/1949 | Olin | 558/445 |
| 4,255,448 A * | 3/1981 | Fariello | 424/315 |
| 4,375,477 A | 3/1983 | Bey et al. | 514/561 |
| 4,703,061 A | 10/1987 | Kameyama et al. | 514/551 |
| 4,906,779 A | 3/1990 | Weber et al. | |
| 4,965,283 A | 10/1990 | Klessing et al. | 514/422 |
| 5,252,576 A | 10/1993 | Sakata et al. | |
| 5,362,902 A | 11/1994 | Barnish et al. | 560/13 |
| 5,648,369 A | 7/1997 | Kadaba | 514/357 |
| 6,306,909 B1 * | 10/2001 | Weaver et al. | 514/561 |

FOREIGN PATENT DOCUMENTS

| | | |
|---|---|---|
| DE | 4300912 A1 | 7/1994 |
| EP | 0343050 B1 | 12/1992 |
| EP | 0718280 A2 | 6/1996 |
| GB | 953997 | 4/1964 |
| GB | 2327672 | 2/1999 |
| JP | 61236724 | 10/1986 |
| WO | WO-95/12400 A1 | 5/1995 |
| WO | WO-95/19346 A1 | 7/1995 |
| WO | WO-96/17832 A1 | 6/1996 |
| WO | WO-98/27972 A2 | 7/1998 |
| WO | WO98/40055 * | 9/1998 |
| WO | WO98/40055 A2 | 9/1998 |
| WO | WO98/40055 A3 | 9/1998 |
| WO | WO-99/52493 A3 | 10/1999 |
| WO | WO-9951572 A1 | 10/1999 |
| WO | WO-00/06570 A1 | 2/2000 |
| WO | WO-00/11952 A1 | 3/2000 |
| WO | WO-00/50043 A1 | 8/2000 |
| WO | WO-00/56715 A1 | 9/2000 |
| WO | WO-01/51490 A1 | 7/2001 |

OTHER PUBLICATIONS

Huxtable et al., CAPLUS Abstract 89:70974, 1978.*
Abdul-Ghani, A. et al. "The Anti-Epileptic Effect of 3-Aminopropylarsonate on Electrically-Kindled and NMDA-Kindled Amygdala" *Brain Research* 742(1-2):305-312 (1996).
Beyer, C. et al. "Prevention of the Convulsant and Hyperalgesic Action of Strychnine by Intrathecal Glycine and Related Amino Acids" *Pharmacol Biochem Behav,* 29:73-78 (1988).
Bogousslavsky, J. et al. "Persistent Worsening of Stroke Sequelae After Delayed Seizures" *Arch. Neurol.* 49:385-389 (1992). AMA Journals [online]. Chicago, IL, U.S.A.: Am. Med. Ass. [retrie-ved Sep. 13, 2000]. Dialog Information Services, Palo Alto, CA, USA. Dialog Acc No. 00055476.
Bonati, Chemical abstract 56:7247-7248 1962.
Camaggi, Chemical abstract 125:168644 1996.
Carran, John R. et al. "β-Amino Acids, a Novel Class of Antiictogenic/Antiepileptogenic Agents" *Epilepsia* 39(Suppl. 6):40 (1998).
Fariello, R. "Action of Inhibitory Amino Acids on Acute Epileptic Foci: An Electrographic Study" *Experimental Neurology* 66:55-63 (1979).
Gusel, V.A. "The Effects of GABA-Positive Drugs on the Primary and "Mirror" Epileptogenic Foci in the Rat Hippocamp" *Farmakol Toksikol (USSR)* 49(3):96-100 (1986) (Eng. Abstr. pg 100).
Horton, R. et al. "Convulsant and Anticonvulsant Actions in DBA/2 Mice of Compounds Blocking the Reuptake of GABA" *European Journal of Pharmacology* 59:75-83 (1979).
Jefferys, J.G.R. "Nonsynaptic Modulation of Neuronal Activity in the Brain: Electric Currents and Extracellular Ions" *Physiological Reviews* 75(4):689-723 (Oct. 1995).
Kouyoumdjian, J.C. et al. "Anticonvulsant Activity of Muscimol and γ-Aminobutyric Acid Against Pyridoxal Phosphate-Induced Epileptic Seizures" *J Neurochem* 36(1):251-257 (1981).
Krogsgaard-Larsen, P. et al. "$GABA_A$ Receptor Agonists, Partial Agonists, and Antagonists. Design and Therapeutic Prospects" *Journal of Medicinal Chemistry* 37(16):2489-2505 (1994).

(Continued)

Primary Examiner—Deepak Rao
(74) *Attorney, Agent, or Firm*—Davidson, Davidson & Kappel LLC

(57) ABSTRACT

Methods and compounds useful for the inhibition of convulsive disorders, including epilepsy, are disclosed. The methods and compounds of the invention inhibit or prevent ictogenesis and epileptogenesis. Methods for preparing the compounds of the invention are also described.

51 Claims, 4 Drawing Sheets

OTHER PUBLICATIONS

Lambert, D.M. et al. "Dérivés simples d'acides aminés neurotransmetteurs. Evaluation anticonvulsivante de dérivés amides, carbamates et esters de la glycine et de la β-alanine" *J. Pharm. Belg.* 50(2-3):194-203 (1995) (with English abstract on page 194).

Leeson, P.D. et al. "The Glycine Site on the NMDA Receptor: Structure-Activity Relationships and Therapeutic Potential" *Journal of Medicinal Chemistry* 37(24):4053-4067 (1994).

Liu, Q-R. et al. "Cloning and Expression of a cDNA Encoding the Transporter of Taurine and β-alanine in Mouse Brain" *Proc. Natl. Acad. Sci. USA* 89:12145-12149 (1992).

Macon, JB. et al. "Responses of Somatosensory Cortical Neurons to Inhibitory Amino Acids During Topical and Iontophoretic Application of Epileptogenic Agents" *Electroencephalography Clin.I Neurophysiol* 47:41-51 (1979).

Milne, PH. "The Design and Synthesis of Antiepileptic Agents Based on Neurotransmitter and Neural Metal-Mediated Inhibition" *Disseration Abstracts International* 59/06-B:2767 (1998) (abstr) Diss. Abstr Online. Ann Arbor, MI, USA: University Microfilms International [retrieved on Sep. 13, 2000]. Dialog Information Services, Palo Alto, CA, USA. Dialog Acc. No. 01650054.

Nanavati, S.M. et al. "Design of Potential Anticonvulsant Agents: Mechanistic Classification of GABA Aminotransferase Inactivators" *Journal of Medicinal Chemistry* 32(11):2413-2421 (1989).

N'Goka, V. et al. "GABA-Uptake Inhibitors: Construction of a General Pharmacophore Model and Successful Prediction of a New Representative" *J. Med. Chem.* 34:2547-2557 (1991).

Okamoto, K. et al. "Effects of Amino Acids and Convulsants on Spontaneous Action Potentials in Cerebellar Cortex Slices" *Br. J. Pharmac.* 57:3-15 (1976).

Paiva, M.Q. et al. "The Kinetic Characteristics of the Extraneuronal O-methlyating System of the Dog Saphenous Vein and the Supersensitivity to Catecholamines Caused by its Inhibition" *Arch Pharmacol* 327:48-55 (1984).

Sangiah, S. "Effects of Glycine and Other Inhibitory Amino Acid Neurotransmitters on Strychnine Convulsive Threshold in Mice" *Vet. Hum. Toxicol.* 27(2):97-99 (1985).

Scanziani, M. et al. "Role of Excitatory Amino Acid and $GABA_B$ Receptors in the Generation of Epileptiform Activity in Disinhibited Hippocampal Slice Cultures" *Neurosci* 61(4):823-832 (1994).

Stasheff, Steven F. et al. "NMDA Antagonists Differentiate Epileptogenesis from Seizure Expression in an in Vitro Model" *Science* 245:648-651 (Aug. 11, 1989).

Sur, R. N. et al. "Some Central Actions of β-Alanine" *Indian Journal of Experimental Biology* 15:634-638 (1977).

Szkaradzinska, M.B. et al. "Two Cyclic Dipeptide Anticonvulsants: *cyclo*-Glycyl-L-phenylglycine (1) and *cyclo*-L-Alanyl-D-phenylglycine (2)" *Acta Crystallographica* C50:565-569 (1994).

Testa, Chemical abstract 55:27004 1961.

Tsukada, Y. et al. "Suppressive Effects of Various Amino Acids against Ouabain-Induced Seizures in Rats" *The Canadian Journal of Neurological Sciences* Nov. 214-221 (1974).

Watson, Craig "Status Epilepticus. Clinical Features, Pathophysiology, and Treatement" *West J. Med.* 155:626-631 (Dec. 1991).

Wood, J.D. et al. "Comparison of GABA Uptake by Brain and Kidney Preparations" *Amino Acids* 1:67-72 (1991).

Wu, F-S. et al. "Dual Activation of $GABA_A$ and Glycine Receptors by β-alanine: Inverse Modulation by Progesterone and 5α-pregnan-3α-ol-20-one" *Eur J Pharmacol.* 246:239-246 (1993).

Bigge, C.F. et al. "Synthesis of 1,4,7,8,9,10-hexahydro-9-methyl-6nitropyrido[3,4-*f*]-quinoxaline-2,3-dione and related quinoxalinediones: characterization of α-amino-3-hydroxy-5-methyl-4-isoxazolepropionic acid (and *N*-methyl-D-aspartate) receptor and anticonvulsant activity." *J. Med. Chem.* 38:3720-3740 (1995).

Ho, B. et al. "Synthesis and structure-activity relationships of potential anticonvulsants based on 2-piperidinecarboxylic acid and related pharmacophores." *Eur. J. Med. Chem.* 36:265-286 (2001).

Ling, R. et al. "Synthesis of 4-alkyl-pyrrolidine-3-carboxylic acid stereoisomers." *Tetrahedron* 57:6579-6588 (2001).

Baker, B.R., et al., "Irreversible Enzyme Inhibitors. LXXX.[1,2] Inhibitors of Thymidine Phosphorylase. VI.[2] Hydrophobic Bonding with 6 Substituents on the Acidic 5-Nitro- and 5- Bromouracils," *J. Med. Chem.,* vol. 10(3):316-320 (1967).

Huxtable, R., et al., "The prolonged anticonvulsant action of taurine on genetically determined seizure-susceptibility," *CAPLUS,* Accession No. 1978:470974, 1 page (1978).

Connolly, Gerald P., et al., "Uridine and its nucleotides: biological actions, therapeutic potentials," *TiPS,* vol. 20:218-225 (1999).

Matsui, Masaki, et al., "Ozonolysis of Substituted Uracils," *J. Org. Chem.,* vol. 55:1396-1399 (1990).

Skulnick, Harvey I., et al., "Pyrimidinones. 3. N-Substituted 6-Phenylpyrimidinones and Pyrimidinediones with Diuretic/Hypotensive and Antiinflammatory Activity," *J. Med. Chem.,* vol. 29:1499-1504 (1986).

Tateoka, Yuji, et al., "Potentiating Effects of $N^1$, $N^3$-Diallyluracil, $N^1$, $N^3$-Diallylthymine and $N^1$, $N^{3\text{-Diallyl-6-methyluracil}}$ on Pentobarbital-Induced Sleep and Diazepam-Induced Motor Incoordination," *Chem. Pharm. Bull.,* vol. 35(12):4928-4934 (1987).

Temkin, Nancy R., et al., "Antiepileptogenic Agents, How Close Are We?" *Drugs,* vol. 61(8):1045-1055 (2001).

European Search Report Application No. 98910555.6, dated Nov. 16, 2005.

* cited by examiner

ONE POT SYNTHESIS OF BETA-ARYL-BETA-AMINO ACIDS:

ANTI-EPILEPTOGENIC AGENTS

RELATED APPLICATIONS

This application is a divisional application of Ser. No. 09/041,371 filed on Mar. 11, 1998 now U.S. Pat. No. 6,306,909 which claims benefit of priority under 35 U.S.C. 119(e) to co-pending U.S. Provisional Application Nos. 60/041,140 filed Mar. 12, 1997, and 60/073,536 filed Feb. 3, 1998. The contents of both these provisional applications is hereby incorporated by reference.

BACKGROUND OF THE INVENTION

Epilepsy is a serious neurological condition, associated with seizures, that affects hundreds of thousands of people worldwide. Clinically, a seizure results from a sudden electrical discharge from a collection of neurons in the brain. The resulting nerve cell activity is manifested by symptoms such as uncontrollable movements.

A seizure is a single discrete clinical event caused by an excessive electrical discharge from a collection of neurons through a process termed "ictogenesis." As such, a seizure is merely the symptom of epilepsy. Epilepsy is a dynamic and often progressive process characterized by an underlying sequence of pathological transformations whereby normal brain is altered, becoming susceptible to recurrent seizures through a process termed "epileptogenesis." While it is believed that ictogenesis and epileptogenesis have certain biochemical pathways in common, the two processes are not identical. Ictogenesis (the initiation and propagation of a seizure in time and space) is a rapid and definitive electrical/chemical event occurring over seconds or minutes. Epileptogenesis (the gradual process whereby normal brain is transformed into a state susceptible to spontaneous, episodic, time-limited, recurrent seizures, through the initiation and maturation of an "epileptogenic focus") is a slow biochemical and/or histological process which generally occurs over months to years. Epileptogenesis is a two phase process. Phase 1 epileptogenesis is the initiation of the epileptogenic process prior to the first seizure, and is often the result of stroke, disease (e.g., meningitis), or trauma, such as an accidental blow to the head or a surgical procedure performed on the brain. Phase 2 epileptogenesis refers to the process during which brain which is already susceptible to seizures, becomes still more susceptible to seizures of increasing frequency and/or severity. While the processes involved in epileptogenesis have not been definitively identified, some researchers believe that upregulation of excitatory coupling between neurons, mediated by N-methyl-D-aspartate (NMDA) receptors, is involved. Other researchers implicate downregulation of inhibitory coupling between neurons, mediated by gamma-amino-butyric acid (GABA) receptors.

Although epileptic seizures are rarely fatal, large numbers of patients require medication to avoid the disruptive, and potential dangerous, consequences of seizures. In many cases, medication is required for extended periods of time, and in some cases, a patient must continue to take prescription drugs for life. Furthermore, drugs used for the management of epilepsy have side effects associated with prolonged usage, and the cost of the drugs can be considerable.

A variety of drugs are available for the management of epileptic seizures, including older anticonvulsant agents such as phenytoin, valproate and carbamazepine (ion channel blockers), as well as newer agents such as felbamate, gabapentin, and tiagabine. β-Alanine has been reported to have anticonvulsant activity, as well as NMDA inhibitory activity and GABAergic stimulatory activity, but has not been employed clinically. Currently available accepted drugs for epilepsy are anticonvulsant agents, where the term "anticonvulsant" is synonymous with "anti-seizure" or "anti-ictogenic"; these drugs can suppress seizures by blocking ictogenesis, but it is believed that they do not influence epilepsy because they do not block epileptogenesis. Thus, despite the numerous drugs available for the treatment of epilepsy (i.e., through suppression of the convulsions associated with epileptic seizures), there are no generally accepted drugs for the treatment of the pathological changes which characterize epileptogenesis. There is no generally accepted method of inhibiting the epileptogenic process and there are no generally accepted drugs recognized as anti-epileptogenic.

SUMMARY OF THE INVENTION

This invention relates to methods and compounds useful for the treatment and/or prevention of convulsive disorders, including epilepsy.

In one aspect, the invention provides a method for inhibiting epileptogenesis in a subject. The method includes the step of administering to a subject in need thereof an effective amount of an agent which modulates a process in a pathway associated with epileptogenesis such that epileptogenesis is inhibited in the subject. In preferred embodiments, In another aspect, the invention provides a method for inhibiting epileptogenesis in a subject. The method includes the step of administering to a subject in need thereof an effective amount of an agent which antagonizes an NMDA receptor and augments endogenous GABA inhibition, such that epileptogenesis is inhibited in the subject. In preferred embodiments, the agent antagonizes an NMDA receptor by binding to the glycine binding site of the NMDA receptors. In preferred embodiments, the agent augments GABA inhibition by decreasing glial GABA uptake. In certain preferred embodiments, the agent comprises a pharmacophore which both antagonizes an NMDA receptor and augments endogenous GABA inhibition. The agent can be administered orally and, in certain embodiments, after the step of oral administration, the agent can be transported into the nervous system of the subject by an active transport shuttle mechanism. In preferred embodiments, the anti-epileptogenic agent is a β-amino anionic compound, in which an anionic moiety is selected from the group consisting of carboxylate, sulfate, sulfonate, sulfinate, sulfamate, tetrazolyl, phosphate, phosphonate, phosphinate, and phosphorothioate. In certain embodiments, the agent is a β-amino acid, but is preferably not β-alanine.

In another aspect, the invention provides a method for inhibiting epileptogenesis in a subject. The method includes the step of administering to a subject in need thereof an effective amount of a compound of the formula:

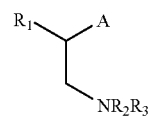

in which A is an anionic group at physiological pH; $R_1$ is alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, halogen, carboxyl, alkoxycarbonyloxy, aryloxycarbonyloxy or aminocarbonyl; and $R_2$ and $R_3$ are each independently hydrogen, alkyl, alkenyl, alkynyl, cycloalkyl, aryl, alkylcarbonyl, arylcarbonyl, alkoxycarbonyl, or aryloxycarbonyl; or $R_2$ and $R_3$, taken together with the nitrogen to which they are attached, form an unsubstituted or substituted heterocycle having from 3 to 7 atoms in the heterocyclic ring; or a pharmaceutically acceptable salt thereof; such that epileptogenesis is inhibited.

In another aspect, the invention provides a method for inhibiting epileptogenesis in a subject. The method includes the step of administering to a subject in need thereof an effective amount of a compound represented by the formula:

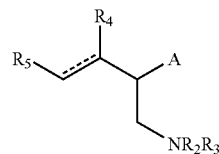

in which the dashed line represents an optional single/double bond; A is an anionic group at physiological pH; $R_2$ and $R_3$ are each independently hydrogen, alkyl, alkenyl, alkynyl, cycloalkyl, aryl, alkylcarbonyl, arylcarbonyl, alkoxycarbonyl, or aryloxycarbonyl; or $R_2$ and $R_3$, taken together with the nitrogen to which they are attached, form an unsubstituted or substituted heterocycle having from 3 to 7 atoms in the heterocyclic ring; $R_4$ and $R_5$ are each independently hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, alkoxycarbonyl, aryloxycarbonyl; or $R_4$ and $R_5$, taken together, form a substituted or unsubstituted carbocyclic or heterocyclic ring having from 5 to 15 atoms in the ring; or a pharmaceutically acceptable salt thereof; such that epileptogenesis is inhibited.

In another aspect, the invention provides a method for inhibiting a convulsive disorder in a subject. The method includes the step of administering to a subject in need thereof an effective amount of a β-amino anionic compound such that the convulsive disorder is inhibited; with the proviso that the β-amino anionic compound is not β-alanine or taurine.

In another aspect, the invention provides an anti-epileptogenic compound of the formula

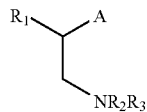

in which A is an anionic group at physiological pH;

$R_1$ is alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, nitro, thiol, thiolalkyl, halogen, carboxyl, alkoxycarbonyloxy, aryloxycarbonyloxy or aminocarbonyl; and $R_2$ and $R_3$ are each independently hydrogen, alkyl, alkenyl, alkynyl, cycloalkyl, aryl, alkylcarbonyl, arylcarbonyl, alkoxycarbonyl, or aryloxycarbonyl; or $R_2$ and $R_3$, taken together with the nitrogen to which they are attached, form an unsubstituted or substituted heterocycle having from 3 to 7 atoms in the heterocyclic ring; or a pharmaceutically acceptable salt thereof; wherein the anti-epileptogenic compound has anti-epileptogenic activity. In preferred embodiments, A represents carboxylate. In certain preferred embodiments, the compound is selected from the group consisting of α-cyclohexyl-β-alanine, α-(4-tert-butylcyclohexyl)-β-alanine, α-(4-phenylcyclohexyl)-β-alanine, α-cyclododecyl-β-alanine, β-(p-methoxyphenethyl)-β-alanine, and β-(p-methylphenethyl)-β-alanine, and pharmaceutically-acceptable salts thereof; or the compound is selected from the group consisting of β-(4-trifluoromethylphenyl)-β-alanine and β-[2-(4-hydroxy-3-methoxyphenyl)ethyl]-β-alanine, and pharmaceutically-acceptable salts thereof; or the compound is selected from the group consisting of β-(3-pentyl)-β-alanine and β-(4-methylcyclohexyl)-β-alanine, and pharmaceutically-acceptable salts thereof.

In still another aspect, the invention provides a dioxapiperazine compound of the formula

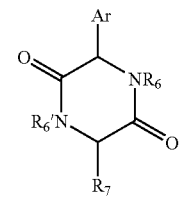

in which

Ar represents an unsubstituted or substituted aryl group;

$R_6$ and $R_6'$ are each independently hydrogen, alkyl, alkylcarbonyl, arylcarbonyl, alkoxycarbonyl or aryloxycarbonyl; and $R_7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is hydrogen or a heterocyclic moiety selected from the group consisting of thiazolyl, triazolyl, and imidazolyl;

with the proviso that if Ar is an unsubstituted phenyl group, $R_7$ is not hydrogen, methyl or phenyl;

or a pharmaceutically-acceptable salt thereof.

In another aspect, the invention provides a method for inhibiting a convulsive disorder in a subject. The method includes the step of administering to a subject in need thereof an effective amount of an agent which a) blocks sodium or calcium ion channels, or opens potassium or chloride ion channels; and b) has at least one activity selected from the group consisting of NMDA receptor antagonism; augmentation of endogenous GABA inhibition; calcium binding; iron binding; zinc binding; NO synthase inhibition; and antioxidant activity; such that epileptogenesis and ictogenesis is inhibited in the subject. In preferred embodiments, the agent antagonizes NMDA receptors by binding to the NMDA receptors (e.g., by binding to the glycine binding site of the NMDA receptors); the agent augments GABA inhibition by decreasing glial GABA uptake; the agent is administered orally; the agent in a pharmaceutically acceptable vehicle; the agent comprises a dioxapiperazine moiety; and/or the subject is a human.

In another aspect, the invention provides a method for inhibiting a convulsive disorder. The method includes the step of administering to a subject in need thereof an effective amount: of a compound represented by the formula

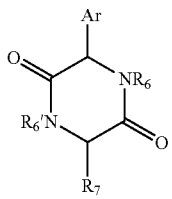

in which

Ar represents an unsubstituted or substituted aryl group;

$R_6$ and $R_6'$ are each independently hydrogen, alkyl, alkylcarbonyl, arylcarbonyl, alkoxycarbonyl or aryloxycarbonyl; and $R_7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is hydrogen or a heterocyclic moiety selected from the group consisting of thiazolyl, triazolyl, and imidazolyl;

with the proviso that if Ar is unsubstituted phenyl, $R_7$ is not hydrogen, methyl or unsubstituted phenyl;

or a pharmaceutically acceptable salt thereof;

such that the convulsive disorder is inhibited.

In another aspect, the invention provides a compound of the formula

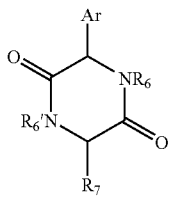

in which

Ar represents an unsubstituted or substituted aryl group;

$R_6$ is hydrogen or alkyl, alkylcarbonyl, arylcarbonyl, alkoxycarbonyl or aryloxycarbonyl;

$R_6'$ is selected from the group consisting of an antioxidant moiety, an NMDA antagonist, an NO synthase inhibitor, an iron chelator moiety, a CA(II) chelator moiety, and a Zn(II) chelator moiety; and $R_7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is a heterocyclic moiety selected from the group consisting of thiazolyl, triazolyl, and imidazolyl;

or a pharmaceutically-acceptable salt thereof. In preferred embodiments, $R_6'$ is D-α-aminoadipyl and/or $R_7$ is mercaptomethyl.

In another aspect, the invention provides a method for concomitantly inhibiting epileptogenesis and ictogenesis, the method including the step of administering to a subject in need thereof an effective amount of a compound of the formula:

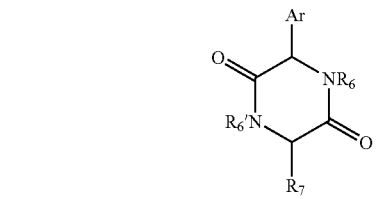

in which

Ar represents an unsubstituted or substituted aryl group;

$R_6$ is hydrogen or alkyl, alkylcarbonyl, arylcarbonyl, alkoxycarbonyl or aryloxycarbonyl;

$R_6'$ is selected from the group consisting of an antioxidant moiety, an NMDA antagonist, an NO synthase inhibitor, an iron chelator moiety, a Ca(II) chelator moiety, and a Zn(II) chelator moiety; and $R_7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is a heterocyclic moiety selected from the group consisting of thiazolyl, triazolyl, and imidazolyl;

or a pharmaceutically-acceptable salt thereof;

such that epileptogenesis is inhibited.

In another aspect, the invention provides a method for treating a disorder associated with NMDA receptor antagonism, the method including the step of administering to a subject in need thereof an effective amount of a compound of the formula:

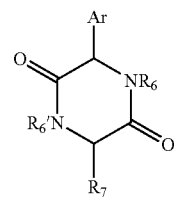

in which

Ar represents an unsubstituted or substituted aryl group;

$R_6$ is hydrogen or alkyl, alkylcarbonyl, arylcarbonyl, alkoxycarbonyl or aryloxycarbonyl;

$R_6'$ is an NMDA antagonist moiety;

$R_7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is a heterocyclic moiety selected from the group consisting of thiazolyl, triazolyl, and imidazolyl;

or a pharmaceutically acceptable salt thereof; and such that the disorder associated with NMDA receptor antagonism is treated.

In another aspect, the invention provides a method for preparing a β-amino carboxyl compound represented by formula VI:

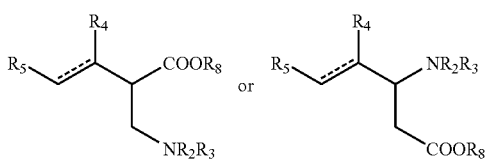

in which
the dashed line represents an optional single/double bond;
$R_2$ and $R_3$ are each independently hydrogen, alkyl, alkenyl, alkynyl, cycloalkyl, aryl, alkylcarbonyl, arylcarbonyl, alkoxycarbonyl, or aryloxycarbonyl; or $R_2$ and $R_3$, taken together with the nitrogen to which they are attached, form an unsubstituted or substituted heterocycle having from 3 to 7 atoms in the heterocyclic ring;
$R_4$ and $R_5$ are each independently hydrogen, alkyl, alkenyl, alkynyl, cycloalkyl, aryl, alkylcarbonyl, arylcarbonyl, alkoxycarbonyl, aryloxycarbonyl, amino, hydroxy, cyano, carboxyl, alkoxycarbonyl, or aryloxycarbonyl; or $R_4$ and $R_5$, taken together form a substituted or unsubstituted carbocyclic or heterocyclic ring having from 5 to 15 atoms in the ring; and
$R_8$ is hydrogen, alkyl, aryl, or an organic or inorganic salt-forming cation. The method includes the step of reacting a compound of formula VII

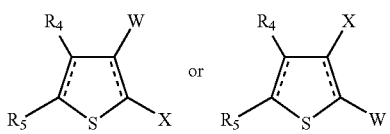

in which
the dashed lines each represent an optional single bond;
X is nitro, azido, or $NR_2R_3$, wherein $R_2$ and $R_3$ are defined above;
W is —CN or —$COOR_8$;
$R_4$ and $R_5$ are as defined above; and
$R_8$ is hydrogen, alkyl, aryl, or an organic or inorganic salt-forming cation;
under reductive desulfurization conditions such that the β-amino carboxyl compound is formed.

In another aspect, the invention provides a method for preparing a β-amino carboxyl compound represented by formula VIII:

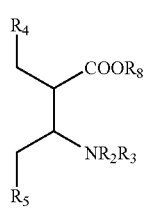

in which
$R_2$ and $R_3$ are each independently hydrogen, alkyl, alkenyl, alkynyl, cycloalkyl, aryl, alkylcarbonyl, arylcarbonyl, alkoxycarbonyl, or aryloxycarbonyl; or $R_2$ and $R_3$, taken together with the nitrogen to which they are attached, form an unsubstituted or substituted heterocycle having from 3 to 7 atoms in the heterocyclic ring;
$R_4$ and $R_5$ are each independently hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, alkoxycarbonyl, aryloxycarbonyl; or $R_4$ and $R_5$, taken together, form a substituted or unsubstituted carbocyclic or heterocyclic ring having from 5 to 15 atoms in the ring; and
$R_8$ is hydrogen, alkyl, aryl, or an organic or inorganic salt-forming cation. The method includes reacting a compound of formula IX

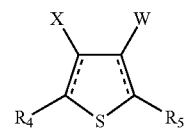

in which
the dashed lines each represent an optional single/double bond;
X is nitro, azido, or $NR_2R_3$, wherein $R_2$ and $R_3$ are defined above;
W is —CN or —$COOR_8$;
$R_8$ is hydrogen, alkyl, aryl, or an organic or inorganic salt-forming cation; and
$R_4$ and $R_5$ are as defined above; under reductive desulfurization conditions such that the β-amino carboxyl compound of Formula VIII is formed;
with the proviso that if W is —CN, the method comprises the further step of acidification.

In still another aspect, the invention provides a method for inhibiting epileptogenesis and ictogenesis in a subject. The method includes the step of administering to a subject in need thereof an effective amount of an agent represented by the formula A-B, in which A is a domain having sodium or calcium ion channel blocking activity, or A has potassium or chloride channel opening activity; and B is a domain having has at least one activity selected from the group consisting of NMDA receptor antagonism; augmentation of endogenous GABA inhibition; calcium binding; iron binding; zinc binding; NO synthase inhibition; and antioxidant activity; such that epileptogenesis is inhibited in the subject. In preferred embodiments, the domains A and B of the agent are covalently linked. In a preferred embodiment, A is a dioxapiperazine moiety.

In yet another aspect, the invention provides a method for inhibiting epileptogenesis. The method includes the step of administering to a subject in need thereof an effective amount of a compound represented by the formula:

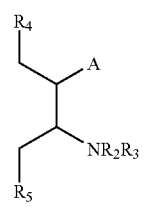

in which

A is an anionic group at physiological pH;

R$_2$ and R$_3$ are each independently hydrogen, alkyl, alkenyl, alkynyl, cycloalkyl, aryl, alkylcarbonyl, arylcarbonyl, alkoxycarbonyl, or aryloxycarbonyl; or R$_2$ and R$_3$, taken together with the nitrogen to which they are attached, form an unsubstituted or substituted heterocycle having from 3 to 7 atoms in the heterocyclic ring;

R$_4$ and R$_5$ are each independently hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, alkoxycarbonyl, or aryloxycarbonyl; or R$_4$ and R$_5$, taken together, form a substituted or unsubstituted carbocyclic or heterocyclic ring having from 5 to 15 atoms in the ring;

or a pharmaceutically acceptable salt thereof;

such that epileptogenesis is inhibited.

In another aspect, the invention provides a method for inhibiting a neurological condition in a subject. The method includes the step of administering to a subject in need thereof an effective amount of an agent which antagonizes an NMDA receptor and augments endogenous GABA inhibition, such that the neurological condition is inhibited in the subject, wherein the neurological condition is selected from the group consisting of stroke, Alzheimer's disease, cancer, and neurodegenerative disease.

In another aspect, the invention provides a method for preparing a β-aryl-β-alanine compound. The method includes the step of reacting an aryl aldehyde with a malonate compound and an ammonium compound, under conditions such that a β-aryl-β-alanine compound is formed.

In another aspect, the invention provides a method for inhibiting epileptogenesis. The method includes the step of administering to a subject in need thereof an effective amount of a compound represented by the formula:

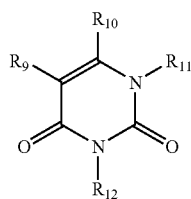

in which

R$_9$ and R$_{10}$ are each independently selected from the group consisting of hydrogen, alkyl, alkenyl, alkynyl, aryl, alkoxy, aryloxy, alkylcarbonyl, arylcarbonyl, alkoxycarbonyl, aryloxycarbonyl, amino, hydroxy, thiol, alkylthiol, nitro, cyano, halogen, carboxyl, alkoxycarbonyloxy, aryloxycarbonyloxy and aminocarbonyl; or R$_9$ and R$_{10}$, together with the two-carbon unit to which they are attached, are joined to form a carbocyclic or heterocyclic ring having from 4 to 8 members in the ring; and R$_{11}$ is hydrogen, alkyl, alkenyl, alkynyl, cycloalkyl, aryl, alkylcarbonyl, arylcarbonyl, alkoxycarbonyl, or aryloxycarbonyl; or R$_{10}$ and R$_{11}$, together with the carbon atom and nitrogen atom to which they are respectively attached, are joined to form a heterocyclic ring having from 4 to 8 members in the ring; and R$_{12}$ is selected from the group consisting of hydrogen, alkyl, aryl and a carbohydrate;

or a pharmaceutically acceptable salt thereof, such that epileptogenesis is inhibited.

In another aspect, the invention provides a method for inhibiting epileptogenesis. The method includes the step of administering to a subject in need thereof an effective amount of a compound represented by the formula:

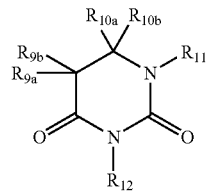

in which

R$_{9a}$, R$_{9b}$, R$_{10a}$, R$_{10b}$ are each independently selected from the group consisting of hydrogen, alkyl, alkenyl, alkynyl, aryl, alkoxy, aryloxy, alkylcarbonyl, arylcarbonyl, alkoxycarbonyl, aryloxycarbonyl, amino, hydroxy, thiol, alkylthiol, nitro, cyano, halogen, carboxyl, alkoxycarbonyloxy, aryloxycarbonyloxy and aminocarbonyl; or R$_{9a}$ and R$_{9b}$, together with the two-carbon unit to which they are attached, are joined to form a carbocyclic or heterocyclic ring having from 4 to 8 members in the ring; or R$_{10a}$ and R$_{10b}$, together with the two-carbon unit to which they are attached, are joined to form a carbocyclic or heterocyclic ring having from 4 to 8 members in the ring; or one of R$_{9a}$ and R$_{9b}$ is joined with one of R$_{10a}$ and R$_{10b}$, together with the two-carbon unit to which they are attached, to form a carbocyclic or heterocyclic ring having from 4 to 8 members in the ring;

R$_{11}$ is hydrogen, alkyl, alkenyl, alkynyl, cycloalkyl, aryl, alkylcarbonyl, arylcarbonyl, alkoxycarbonyl, or aryloxycarbonyl; or one of R$_{10b}$ and R$_{10b}$ is joined with R$_{11}$, together with the carbon atom and nitrogen atom to which they are respectively attached, to form a heterocyclic ring having from 4 to 8 members in the ring; and R$_{12}$ is selected from the group consisting of hydrogen, alkyl, aryl and a carbohydrate (such as a sugar, e.g., ribose or deoxyribose);

or a pharmaceutically acceptable salt thereof;

such that epileptogenesis is inhibited.

In another aspect, the invention provides pharmaceutical compositions of the compounds of the invention.

In another apect, the invention provides a kit comprising a container of a compound of the invention and instructions for administering a therapeutically effective amount of the compound to a subject in need thereof such that epileptogenesis is inhibited in the subject.

It is an object of the present invention to provide novel anti-epileptogenic compounds and methods for inhibiting epileptogenesis.

It is a further object of the invention to provide compounds and methods for treatment of stroke, Alzheimer's disease and neurodegenerative disorders.

It is a further object of the invention to provide novel anticonvulsant agents. It is a further object of the invention to provide compounds and methods for treating stroke and pain.

These and other objects, features, and advantages of the invention will be apparent from the following description and claims.

DETAILED DESCRIPTION OF THE INVENTION

Figure 1:
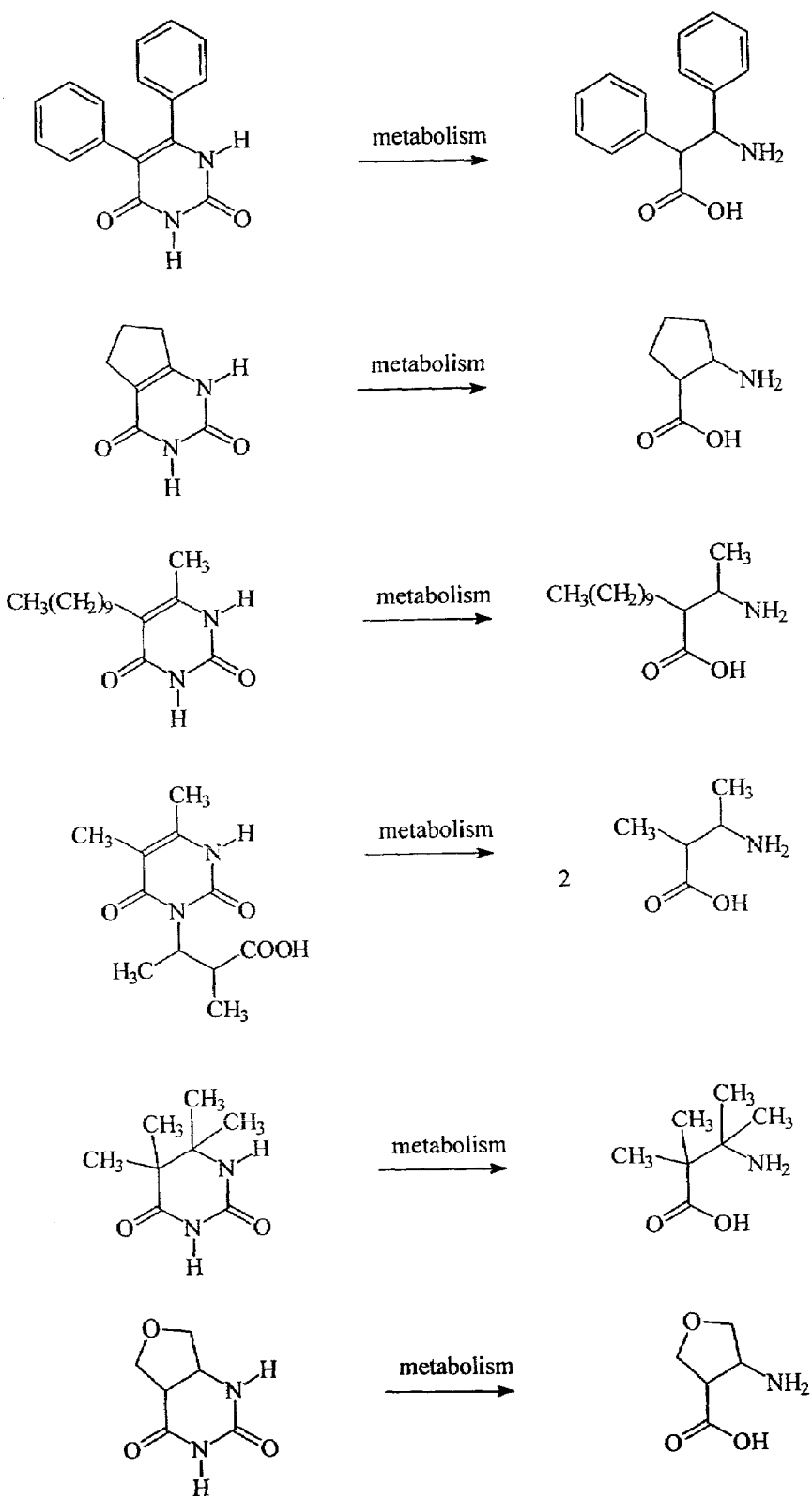
FIG. 1 depicts exemplary pyrimidine and dihydropyrimidine compounds useful in the methods of the invention.

The present invention pertains to methods and agents useful for the treatment of epilepsy and convulsive disorders, for inhibition of epileptogenesis, and for inhibition of ictogenesis; and to methods for preparing the anti-convulsive and anti-epileptogenic agents of the invention. The invention further pertains to pharmaceutical compositions for treatment of convulsive disorders, and to kits including the anti-convulsive compounds of the invention.

Definitions

For convenience, certain terms used in the specification, examples, and appended claims are collected here.

The language "a process in a pathway associated with epileptogenesis," as used herein, refers to a biochemical process or event which takes place during Phase 1 or Phase 2 epileptogenesis and leads to epileptogenic changes in tissue, i.e., in tissues of the central nervous system (CNS), e.g., the brain. Examples of processes in pathways associated with epileptogenesis are discussed in more detail, infra.

The language "a disorder associated with NMDA receptor antagonism," as used herein, refers to any disorder of a subject in which abnormal (e.g., excessive) activity of NMDA receptors can be treated by antagonism of an NMDA receptor. As described above, epilepsy is a disorder associated with excessive NMDA-mediated activity. Other non-limiting examples of disorders associated with excessive NMDA-mediated activity include pain, stroke, anxiety, schizophrenia, other psychoses, cerebral ischemia, Huntington's chorea, motor neuron disease, Alzheimer's disease, AIDS dementia and other disorders (in humans or animals) in which excessive activity of NMDA receptors is a cause, at least in part, of the disorder (see, e.g., Schoepp et al., Eur. J. Pharmacol. 203:237-243 (1991); Leeson et al., J. Med. Chem. 34:1243-1252 (1991); Kulagowski et al., J. Med. Chem. 37:1402-1405 (1994); Mallamo et al., J. Med Chem. 37:4438-4448 (1994); and references cited therein).

The term "convulsive disorder," as used herein, refers to a disorder of a subject in which the subject suffers from convulsions, e.g., convulsions due to epileptic seizure. Convulsive disorders include, but are not limited to, epilepsy and non-epileptic convulsions, e.g., convulsions due to administration of a convulsive agent to the subject.

The term "inhibition of epileptogenesis," as used herein, refers to preventing, slowing, halting, or reversing the process of epileptogenesis, i.e., the changes in brain tissue which result in epileptic seizures.

The term "anti-epileptogenic agent," as used herein, refers to an agent which is capable of inhibiting epileptogenesis when the agent is administered to a subject.

The term "anticonvulsant agent," as used herein, refers to an agent capable of inhibiting (e.g., preventing, slowing, halting, or reversing) ictogenesis when the agent is administered to a subject.

The term "pharmacophore" is known in the art, and, as used herein, refers to a molecular moiety capable of exerting a selected biochemical effect, e.g., inhibition of an enzyme, binding to a receptor, chelation of an ion, and the like. A selected pharmacophore can have more than one biochemical effect, e.g., can be an inhibitor of one enzyme and an agonist of a second enzyme. A therapeutic agent can include one or more pharmacophores, which can have the same or different biochemical activities.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action,* Academic Press, Inc.: San Diego, Calif., 1992, pp. 19-23). A particularly preferred anionic group is a carboxylate.

The term "β-amino anionic compound," as used herein, refers to a compound having an amino group (e.g., $-NR_aR_b$, in which $R_a$ and $R_b$ are each independently hydrogen, alkyl, alkenyl, alkynyl, cycloalkyl, aryl, alkylcarbonyl, arylcarbonyl, alkoxycarbonyl, or aryloxycarbonyl, or $R_a$ and $R_b$, taken together with the nitrogen atom to which they are attached, form a cyclic moiety having from 3 to 8 atoms in the ring) separated from an anionic group by a two-carbon spacer unit. Thus, for example, a amino anionic compound can be represented by the formula A-CHR'CHR'—$NR_aR_b$, in which each R' can independently be hydrogen or any substituent of an alkyl group as defined above, and A is an anionic group. Preferred β-amino anionic compounds include β-amino acids. In certain preferred embodiments, the β-amino anionic compound is not β-alanine or taurine.

The language "reductive desulfurization" is known in the art, and, as used herein, refers to the process of reductively eliminating sulfur from a compound. Conditions for reductive desulfurization are known in the art and include, e.g., treatment with $TiCl_4/LiAlH_4$ or Raney nickel/$H_2$ (for a general reference, see, e.g., Kharash, N. and Meyers, C. Y., "The Chemistry of Organic Sulfur Compounds," Pergamon Press, New York (1966), Vol. 2).

The term "subject" is known in the art, and, as used herein, refers to a warm-blooded animal, more preferably a mammal, including, e.g., non-human animals such as rats, mice, cats, dogs, sheep, horses, cattle, in addition to humans. In a preferred embodiment, the subject is a human.

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably has 20 or fewer carbon atoms in the backbone. Likewise, preferred cycloalkyls have from 4-10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "aryl" as used herein includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively.

As used in the description and drawings herein, an "optional single/double bond" is represented by a solid line together with a dashed line, and refers to a covalent linkage between two carbon atoms which can be either a single bond or a double bond. For example, the structure:

can represent either cyclohexane or cyclohexene.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The terms "heterocyclyl" or "heterocyclic group" refer to 3- to 10-membered ring structures, more preferably 4- to 7-membered rings, which ring structures include one to four heteroatoms. Heterocyclyl groups include pyrrolidine, oxolane, thiolane, piperidine, piperazine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "aryl aldehyde," as used herein, refers to a compound represented by the formula Ar—C(O)H, in which Ar is an aryl moiety (as described above) and —C(O)H is a formyl or aldehydo group. In a preferred embodiment, the aryl aldehyde is a (substituted or unsubstituted) benzaldehyde. A variety of aryl aldehydes are commercially available, or can be prepared by routine procedures from commercially available precursors. Procedures for the preparation of aryl aldehydes include the Vilsmeier-Haack reaction (see, e.g., Jutz, *Adv. Org. Chem.* 9, pt. 1, 225-342 (1976)), the Gatterman reaction (see Truce, *Org. React.* 9, 37-72 (1957)), the Gatterman-Koch reaction (see Crounse, *Org. React.* 5, 290-300 (1949)), and the Reimer-Tiemann reaction (see Wynberg and Meijer, *Org. React.* 28, 1-36 (1982)).

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, alkenes can include either the E- or Z-geometry, where appropriate.

I. Methods for Treating Convulsive Disorders

In one aspect, the invention provides methods for treating convulsive disorders, including epilepsy.

In one embodiment, the invention provides a method for inhibiting epileptogenesis in a subject. The method includes the step of administering to a subject in need thereof an effective amount of an agent which modulates a process in a pathway associated with epileptogenesis, such that epileptogenesis is inhibited in the subject.

As noted above, upregulation of excitatory coupling between neurons, mediated by N-methyl-D-aspartate (NMDA) receptors, and downregulation of inhibitory coupling between neurons, mediated by gamma-amino-butyric acid (GABA) receptors; have both been implicated in epileptogenesis. Other processes in pathways associated with epileptogenesis include release of nitric oxide (NO), a neurotransmitter implicated in epileptogenesis; release of calcium ($Ca^{2+}$), which may mediate damage to neurons when released in excess; neurotoxicity due to excess zinc ($Zn^{2+}$); neurotoxicity due to excess iron ($Fe^{2+}$); and neurotoxicity due to oxidative cell damage. Accordingly, in preferred embodiments, an agent to be administered to a subject to inhibit epileptogenesis preferably is capable of inhibiting one or more processes in at least one pathway associated with epileptogenesis. For example, an agent useful for inhibition of epileptogenesis can reduce the release of, or attenuate the epileptogenic effect of, NO in brain tissue; antagonize an NMDA receptor; augment endogenous GABA inhibition; block voltage-gated ion channels; reduce the release of, reduce the free concentration of (e.g., by chelation), or otherwise reduce the epileptogenic effect of cations including $Ca^{2+}$, $Zn^{2+}$, or $Fe^{2+}$; inhibit oxidative cell damage; or the like. In certain preferred embodiments, an agent to be administered to a subject to inhibit epileptogenesis is capable of inhibiting at least two processes in at least one pathway associated with epileptogenesis.

Non-limiting examples of pharmacophores which can modulate a process in a pathway associated with epileptogenesis include:

Inhibitors of NO synthase: L-arginine and alkylated derivatives thereof;

Antagonization of NMDA receptors: (R)-α-amino acids; for a general review of inhibitors of the NMDA receptor, see Leeson, P. D. and Iverson, L. L., *J. Med. Chem.* (1994) 37:4053-4067;

Augmentation of endogenous GABA inhibition: inactivators of GABA aminotransferase (such as gamma-vinyl-GABA; for a review of GABA receptor agonists and antagonists, see Krogsgaard-Larsen, P., et al., *J. Med. Chem.* (1994) 37:2489-2505);

Chelators of $Ca^{2+}$, $Zn^{2+}$, or $Fe^{2+}$: EDTA, EGTA, TNTA, 2,2-bipyridine-4,4,-dicarboxylate, enterobactin, porphyrins, crown ethers, azacrown ethers; and Antioxidants: vitamins C, and E; carotenoids such as β-carotene; butylated phenols, Trolox (a tocopherol analog), selenium; glutathione.

In one preferred embodiment, the agent antagonizes an NMDA receptor and augments endogenous GABA inhibition. In certain preferred embodiments, the agent is administered orally; preferably, after the step of oral administration, the agent is transported to the nervous system of the subject by an active transport shuttle mechanism. A non-limiting example of an active transport shuttle is the large neutral amino acid transporter, which is capable of transporting amino acids across the blood-brain barrier (BBB).

In another embodiment, the invention provides a method for inhibiting epileptogenesis. The method includes the step of administering to a subject in need thereof an effective amount of a compound of the formula (Formula I):

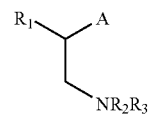

in which A is an anionic group at physiological pH; $R_1$ is alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, thiol, alkylthiol, nitro, cyano, halogen, carboxyl, alkoxycarbonyloxy, aryloxycarbonyloxy or aminocarbonyl; and $R_2$ and $R_3$ are each independently hydrogen, alkyl, alkenyl, alkynyl, cycloalkyl, aryl, alkylcarbonyl, arylcarbonyl, alkoxycarbonyl, or aryloxycarbonyl; or $R_2$ and $R_3$, taken together with the nitrogen to which they are attached, form an unsubstituted or substituted heterocycle having from 3 to 7 atoms in the heterocyclic ring; or a pharmaceutically acceptable salt thereof, such that epileptogenesis is inhibited. In a preferred embodiment, $R_2$ and $R_3$ are both hydrogen.

In certain embodiments, the compound of Formula I can be represented by the formula (Formula II):

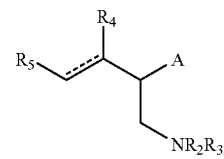

in which the dashed line represents an optional single bond; $R_4$ and $R_5$ are each independently hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, alkoxycarbonyl, aryloxycarbonyl; or $R_4$ and $R_5$, taken together, form a substituted or unsubstituted carbocyclic or heterocyclic ring having from 5 to 15 atoms (more preferably 5 to 8 atoms) in the ring; and A, $R_2$ and $R_3$ are as defined above; or a pharmaceutically acceptable salt thereof, such that epileptogenesis is inhibited.

In another embodiment, the invention provides a method for inhibiting epileptogenesis. The method includes the step of administering to a subject in need thereof an effective amount of a compound represented by the formula (Formula III):

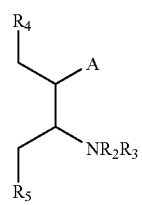

in which A, $R_2$, $R_3$, $R_4$, and $R_5$ are as defined above; or a pharmaceutically acceptable salt thereof; such that epileptogenesis is inhibited. In a preferred embodiment, A is a carboxylate. In a particularly preferred embodiment, A is carboxylate, $R_4$ is hydrogen, and $R_5$ is a (substituted or unsubstituted) aryl group.

In another embodiment, the invention provides a method for inhibiting epileptogenesis. The method includes the step of administering to a subject in need thereof an effective amount of a compound selected from the group consisting of α,α-disubstituted β-alanines, α,β-disubstituted β-alanines, β,β-disubstituted β-alanines, α,β,α-trisubstituted β-alanines, α,β,β-trisubstituted β-alanines, and α,α,β,β-tetrasubstituted β-alanines; or a pharmaceutically acceptable salt thereof, such that epilepogenesis is inhibited.

The step of administering to a subject an anionic compound of the invention, e.g., a compound of Formulas I-III described above, can include administration to the subject of a compound of the invention, e.g., a compound represented by any of Formulas I-III, e.g., a compound in its active form, optionally in a pharmaceutically acceptable carrier (e.g., as described in more detail infra). The step of administering to the subject can also include administering to the subject a compound which is metabolized to an anti-convulsant and/or anti-epileptogenic compound of the invention. For example, the methods of the invention include the use of prodrugs which are converted in vivo to the therapeutic compounds of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the therapeutic compound. For example, an anionic group, e.g., a carboxylate group, can be esterified, e.g., with an ethyl group or a fatty group, to yield a carboxylic ester. When the carboxylic ester is administered to a subject, the ester can be cleaved, enzymatically or non-enzymatically, to reveal the anionic group.

In another illustrative embodiment, the methods of the invention include administering to the subject a derivative of uracil or an analog thereof (including, e.g., substituted pyrimidines, UMP and uridine, or analogs thereof). It has been reported (see, e.g., J. P. Braakhekke et al. *Journal of Neurological Science*, 1987; 78; 71-77) that uracils are enzymatically metabolised to β-alanines via dihydrouracil and β-ureidopropionate. Accordingly, administration of a uracil compound, or a metabolite of a uracil compound such as a dihydrouracil or a β-ureidopropionate, can result in the in vivo formation of an active compound of the invention. Accordingly, in a preferred embodiment, the methods of the invention can include the step of administering to a subject in need thereof an effective amount of a substituted or unsubstituted uracil, dihydrouracil or β-ureidopropionate compound, or a derivative or analog thereof (or a pharmaceutically acceptable salt thereof), in an amount effective to treat a convulsive disorder and/or to inhibit epileptogenesis, e.g., by in vivo conversion of the uracil, dihydrouracil or β-ureidopropionate compound to a β-amino acid compound effective to treat the convulsive disorder.

Thus, in certain embodiments, preferred compounds for administration to a subject (optionally in a pharmaceutically acceptable carrier) include pyrimidines, such as substituted uracils, which can be converted in vivo to β-amino anionic compounds. In a preferred embodiment, the compound can be represented by the formula (Formula V):

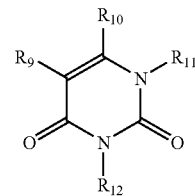

in which $R_9$ and $R_{10}$ are each independently selected from the group consisting of hydrogen, alkyl (including cycloalkyl and aralkyl), alkenyl, alkynyl, aryl, alkoxy, aryloxy, alkylcarbonyl, arylcarbonyl, alkoxycarbonyl, aryloxycarbonyl, amino (including unsubstituted and substituted amino), hydroxy, thiol, alkylthiol, nitro, cyano, halogen, carboxyl, alkoxycarbonyloxy, aryloxycarbonyloxy or aminocarbonyl; or $R_9$ and $R_{10}$, together with the two-carbon unit to which they are attached, are joined to form a carbocyclic or heterocyclic ring having from 4 to 8 members in the ring; and $R_{11}$ is hydrogen, alkyl, alkenyl, alkynyl, cycloalkyl, aryl, alkylcarbonyl, arylcarbonyl, alkoxycarbonyl, or aryloxycarbonyl; or $R_{10}$ and $R_{11}$, together with the carbon atom and nitrogen atom to which they are respectively attached, are joined to form a heterocyclic ring having from 4 to 8 members in the ring; and $R_{12}$ is selected from the group consisting of hydrogen, alkyl, aryl and a carbohydrate (such as a sugar, e.g., ribose or deoxyribose); or a pharmaceutically acceptable salt thereof. In another embodiment, the compound can be represented by the formula (Formula Va):

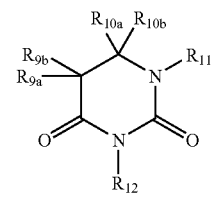

in which $R_{9a}$, $R_{9b}$, $R_{10a}$, $R_{10b}$ are each independently selected from the group consisting of hydrogen, alkyl (including cycloalkyl and aralkyl), alkenyl, alkynyl, aryl, alkoxy, aryloxy, alkylcarbonyl, arylcarbonyl, alkoxycarbonyl, aryloxycarbonyl, amino (including unsubstituted and substituted amino), hydroxy, thiol, alkylthiol, nitro, cyano, halogen, carboxyl, alkoxycarbonyloxy, aryloxycarbonyloxy or aminocarbonyl; or $R_{9a}$ and $R_{9b}$, together with the two-carbon unit to which they are attached, are joined to form a carbocyclic or heterocyclic ring having from 4 to 8 members in the ring; or $R_{10a}$ and $R_{10b}$, together with the two-carbon unit to which they are attached, are joined to form a carbocyclic or heterocyclic ring having from 4 to 8 members in the ring; or one of $R_{9a}$ and $R_{9b}$ is joined with one of $R_{10a}$ and $R_{10b}$, together with the two-carbon unit to which they are attached, to form a carbocyclic or heterocyclic ring having from 4 to 8 members in the ring; $R_{11}$ is hydrogen, alkyl, alkenyl, alkynyl, cycloalkyl, aryl, alkylcarbonyl, arylcarbonyl, alkoxycarbonyl, or aryloxycarbonyl; or one of $R_{10b}$ and $R_{10b}$ is joined with $R_{11}$, together with the carbon atom and nitrogen atom to which they are respectively attached, to form a heterocyclic ring having from 4 to 8 members in the ring; and $R_{12}$ is selected from the group consisting of hydrogen, alkyl, aryl and a carbohydrate (such as a sugar, e.g., ribose or deoxyribose); or a pharmaceutically acceptable salt thereof.

Pyrimidine compounds, such as 5-fluorouracil (5FU), have been used as anti-neoplastic agents. It is generally accepted that the anti-cancer activity of 5FU and similar compounds is due to a "silicide substrate" mechanism in which the 5FU inhibits thymidylate synthase, an enzyme important in DNA synthesis. In preferred embodiments, pyrimidine and dihydropyrimidine compounds administered according to the invention for the treatment of convulsive disorders (inhibition of epileptogenesis) do not significantly inhibit thymidylate synthase. Without wishing to be bound by theory, it is believed that inhibition of thymidylate synthase by pyrimidine compounds is increased by the presence of electronegative groups at the 5-position of the pyrimidine ring (i.e., $R_9$ of Formula 5), and can therefore be decreased by providing such compounds with non-electronegative groups at the 5-position of the pyrimidine ring (i.e., $R_9$ of Formula 5). It is further believed that by providing substituents with sufficient steric bulk to decrease the ability of the pyrimidine compound to bind to thymidylate synthase, inhibition of thymidylate synthase can be decreased. Thus, in preferred embodiments, in a compound of Formula V for administration according to the present invention, $R_9$ is a non-electronegative (i.e., neutral or electropositive) group (e.g., alkyl, aryl, or the like). In preferred embodiments, at least one of $R_9$ and $R_{10}$ of Formula V is a sterically bulky group (e.g., long-chain or branched alkyl, substituted aryl, or the like), or $R_9$ and $R_{10}$ are joined to form a carbocyclic or heterocyclic ring.

Non-limiting examples of pyrimidine and dihydropyrimidine compounds for use according to the invention, together with illustrative active metabolites thereof, are shown in FIG. 1.

The use of substituted or unsubstituted uracils, and derivatives or analogs thereof, may be especially advantageous as certain uracil compounds have been found to have anti-ictogenic properties (only) when tested in an anti-seizure model in rats (see, e.g., Medicinal Chemistry Volume V; W. J. Close, L. Doub, M. A. Spielman; Editor W. H. Hartung; John Wiley and Sons; New York, London; 1961). Thus, the prodrug form of the compound (a uracil) can have anti-seizure activity, while the metabolically-produced β-amino anionic compounds can have anti-epileptogenic and/or anti-convulsive activity. These activities, individually and in combination, can provide effective therapy for convulsive disorders in mammals (including humans).

In certain preferred embodiments, an active agent of the invention antagonizes NMDA receptors by binding to the glycine binding site of the NMDA receptors. In certain preferred embodiments, the agent augments GABA inhibition by decreasing glial GABA uptake. In certain preferred embodiments, the agent is administered orally. In certain preferred embodiments, the method further includes administering the agent in a pharmaceutically acceptable vehicle.

In still another embodiment, the invention provides a method of inhibiting a convulsive disorder. The method includes the step of administering to a subject in need thereof an effective amount of a β-amino anionic compound such that the convulsive disorder is inhibited; with the proviso that the β-amino anionic compound is not β-alanine or taurine.

In another embodiment, the invention provides a method for inhibiting both a convulsive disorder and epileptogenesis in a subject. The method includes the step of administering to a subject in need thereof an effective amount of an agent which a) blocks sodium or calcium ion channels, or opens potassium or chloride ion channels; and b) has at least one activity selected from the group consisting of NMDA receptor antagonism; augmentation of endogenous GABA inhibition; calcium binding; iron binding; zinc binding; NO synthase inhibition; and antioxidant activity; such that epileptogenesis is inhibited in the subject.

Blockers of sodium and/or calcium ion channel activity are well known in the art and can be used as the A moiety in the compounds and methods of the present invention. Similarly, any compound which opens potassium or chloride ion channels can be used as the A moiety in the compounds and methods of the present invention. Antagonist of NMDA receptors and augmenters of endogenous GABA inhibition are also known to one of skill in the art and can be used in the methods and compounds of the invention. For example, 2,3-quinoxalinediones are reported to have NMDA receptor antagonistic activity (see, e.g., U.S. Pat. No. 5,721,234). Exemplary calcium and zinc chelators include moieties known in the art for chelation of divalent cations, including (in addition to those mentioned supra) ethylenediaminetetraacetic acid (EDTA), ethylene glycol bis(beta-aminoethyl ether)-N,N,N',N'-tetraacetic acid, and the like. Exemplary iron chelators include enterobactin, pyridoxal isonicotinyl hydrazones, N,N'-bis(2-hydroxybenzoyl)-ethylenediamine-N,N'-diacetic acid (HBED), 1-substituted-2-alkyl-3-hydroxy-4-pyridones, including 1-(2'-carboxyethyl)-2-methyl-3-hydroxy-4-pyridone, and other moieties known in the art to chelate iron. Compounds which inhibit NO synthase activity are known in the art and include, e.g., Nγ-substituted arginine analogs (especially of the L configuration), including L-Nγ-nitro-arginine (a specific inhibitor of cerebral NO synthase), L-Nγ-amino-arginine, and L-Nγ-alkyl-arginines; or an ester (preferably the methyl ester) thereof. Exemplary antioxidants include ascorbic acid, tocopherols including alpha-tocopherol, and the like.

In another embodiment, the invention provides a method for inhibiting a convulsive disorder. The method includes the step of administering to a subject in need thereof an effective amount of a dioxapiperazine (also known as diketopiperazine) compound represented by the formula (Formula IV):

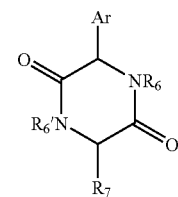

in which Ar represents an unsubstituted or substituted aryl group; $R_7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is a heterocyclic moiety selected from the group consisting of thiazolyl, triazolyl, and imidazolyl; and $R_6$ and $R_6'$ are each independently hydrogen, alkyl, alkylcarbonyl or arylcarbonyl; or a pharmaceutically-acceptable salt thereof; such that the convulsive disorder is inhibited. In a preferred embodiment, $R_7$ is not hydrogen, methyl or phenyl. In a preferred embodiment, the compound is cyclo-D-phenylglycyl-(S-Me)-L-cysteine. For synthesis of dioxapiperazines, see, e.g., Kopple, K. D. et al., *J. Org.*

Chem. 33:862 (1968); Slater, G. P. Chem Ind. (London) 32:1092 (1969); Grahl-Nielsen, O. Tetrahedron Lett. 1969: 2827 (1969). Synthesis of selected dioxapiperazine compounds is described in the Examples, infra.

In another embodiment, the invention provides a method for concurrently inhibiting epileptogenesis and ictogenesis, the method including the step of administering to a subject in need thereof an effective amount of a compound of the formula:

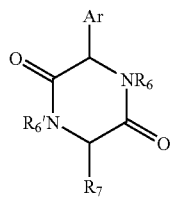

in which Ar represents an unsubstituted or substituted aryl group; $R_7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is a heterocyclic moiety selected from the group consisting of thiazolyl, triazolyl, and imidazolyl; $R_6$ is hydrogen or alkyl, alkylcarbonyl, arylcarbonyl, alkoxycarbonyl or aryloxycarbonyl; and $R_6'$ is selected from the group consisting of an antioxidant moiety, an NMDA antagonist, an NO synthase inhibitor, an iron chelator moiety, a Ca(II) chelator moiety, a Zn(II) chelator moiety, and an antioxidant moiety; or a pharmaceutically-acceptable salt thereof; such that epileptogenesis is inhibited. In certain embodiments, $R_7$ is not hydrogen, methyl or phenyl.

In another embodiment, the invention provides a method for treating a disorder associated with NMDA receptor antagonism. The method includes the step of administering to a subject in need thereof an effective amount of a compound of the formula:

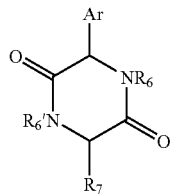

in which Ar represents an unsubstituted or substituted aryl group; $R_7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is a heterocyclic moiety selected from the group consisting of thiazolyl, triazolyl, and imidazolyl; $R_6$ is hydrogen or alkyl, alkylcarbonyl, arylcarbonyl, alkoxycarbonyl or aryloxycarbonyl; and $R_6'$ is an NMDA antagonist moiety; or a pharmaceutically-acceptable salt thereof; such that the disorder associated with NMDA receptor antagonism is treated. In certain embodiments, $R_7$ is not hydrogen, methyl or phenyl.

In yet another embodiment, the invention provides a method for inhibiting ictogenesis and epileptogenesis in a subject. The method includes the step of administering to a subject in need thereof an effective amount of an agent represented by the formula A-B, in which A is a domain having sodium ion channel blocking activity; and B is a domain having at least one activity selected from the group consisting of NMDA receptor antagonism; GABA inhibition augmentation; calcium binding; iron binding; zinc binding; NO synthase inhibition; and antioxidant activity; such that epileptogenesis is inhibited in the subject. In certain preferred embodiments, the domains A and B (e.g., pharmacophores) of the agent are covalently linked. In certain preferred embodiments, A is a dioxapiperazine moiety, a phenytoin moiety, or a carbamazepine moiety.

In another embodiment, the invention provides a method for inhibiting ictogenesis and epileptogenesis in a subject. The method includes the step of administering to a subject in need thereof an effective amount of an agent represented by the formula A-B, in which A is a domain having anti-icotgenenic activity; and B is a domain having at least one activity selected from the group consisting of NMDA receptor antagonism; GABA inhibition augmentation; calcium binding; iron binding; zinc binding; NO synthase inhibition; and antioxidant activity; such that epileptogenesis is inhibited in the subject. In certain preferred embodiments, the domains A and B (e.g., pharmacophores) of the agent are covalently linked. In certain preferred embodiments, A is a dioxapiperazine moiety, a phenytoin moiety, or a carbamazepine moiety.

A hybrid drug according to the invention can be a bifunctional molecule created by connecting an anti-ictogenic moiety with an anti-epileptogenic moiety via a (preferably) covalent linkage (e.g., an amide bond, an ester bond, and the like). The linkage can optionally be cleavable in vivo. The linkage can also include a linker or spacer moiety to provide flexibility or sufficient space between the A and B moieties to permit interaction with the respective moieties to which A and B bind or with which A and B interact. Exemplary linkers include diacids (such as adipic acid), e.g., to link amino-group-containing A and B moieties; or diamines (such as 1,6-hexanediamine), e.g., to link carboxyl-group-containing A and B moieties; or amino acids, e.g., to link an amino-functionalized B moiety to a carboxy-functionalized A moiety (or vice versa). A linker can be selected to provide desired properties according to considerations well known to one of skill in the art. The bifunctional molecule thus targets both ictogenesis and epileptogenesis.

Compounds which find use in the therapeutic methods of the invention can be determined through routine screening assays. For example, the animal model of Phase 1 epileptogenesis described in Example 2, infra, can be employed to determine whether a particular compound has anti-epileptogenic activity against Phase 1 epileptogenesis. Chronic epileptogenesis can be modeled in rats (and candidate compounds screened with) the kindling assay described by Silver et al. (Ann. Neurol. (1991) 29:356). Similarly, compounds useful as anticonvulsants can be screened in conventional animal models, such as the mouse model described in Horton, R. W. et al., Eur. J. Pharmacol. (1979) 59:75-83. Compounds or pharmacophores useful for, e.g., binding to or inhibition of receptors or enzymes can be screened according to conventional methods known to the ordinarily skilled artisan. For example, binding to the GABA uptake receptor can be quantified by the method of Ramsey et al. as modified by Schlewer (Schlewer, J., et al., J. Med. Chem. (1991) 34:2547). Binding to the glycine site on an NMDA receptor can be quantified, e.g., according to the method described in Kemp, A., et al., Proc. Natl. Acad. Sci.

USA (1988) 85:6547. Effect on the voltage-gated Na+ channel can be evaluated in vitro by voltage clamp assay in rat hippocampal slices.

Assays suitable for screening candidate compounds for anticonvulsive and/or anti-epileptogenic activity in mice or rats are described in Examples 4 and 5, infra.

II. Compounds

In another aspect, the invention provides compounds useful for the treatment of epilepsy and convulsive disorders.

In one embodiment, the invention provides an anti-epileptogenic compound of the formula (Formula I)

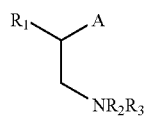

in which A is an anionic group at physiological pH; $R_1$ is alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, halogen, carboxyl, alkoxycarbonyloxy, aryloxycarbonyloxy or aminocarbonyl; and $R_2$ and $R_3$ are each independently hydrogen, alkyl, alkenyl, alkynyl, cycloalkyl, aryl, alkylcarbonyl, arylcarbonyl, alkoxycarbonyl, or aryloxycarbonyl; or $R_2$ and $R_3$, taken together with the nitrogen to which they are attached, form an unsubstituted or substituted heterocycle having from 3 to 7 atoms in the heterocyclic ring; or a pharmaceutically acceptable salt thereof, wherein the anti-epileptogenic compound has anti-epileptogenic activity. In certain preferred embodiments, A represents carboxylate. In certain preferred embodiments, the compound is selected from the group consisting of α-cyclohexyl-β-alanine, α-(4-tert-butylcyclohexyl)-β-alanine, α-(4-phenylcyclohexyl)-β-alanine, α-cyclododecyl-β-alanine, β-(p-methoxyphenethyl)-β-alanine, β-(p-methylphenethyl)-β-alanine, and pharmaceutically-acceptable salts thereof. In other preferred embodiments, the compound is selected from the group consisting of β-(4-trifluoromethylphenyl)-β-alanine and β-[2-(4-hydroxy-3-methoxyphenyl)ethyl]-β-alanine and pharmaceutically-acceptable salts thereof. In still other embodiments, the compound is selected from the group consisting of β-(3-pentyl)-β-alanine and β-(4-methylcyclohexyl)-β-alanine and pharmaceutically-acceptable salts thereof.

In another embodiment, the invention provides a dioxapiperazine compound of the formula (Formula IV)

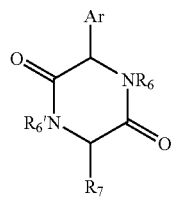

in which Ar represents an unsubstituted or substituted aryl group; $R_7$ is hydrogen, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is hydrogen or a heterocyclic moiety selected from the group consisting of thiazolyl, triazolyl, and imidazolyl; and $R_6$ and $R_6'$ are each independently hydrogen, alkyl, alkylcarbonyl, arylcarbonyl, alkoxycarbonyl or aryloxycarbonyl; or a pharmaceutically-acceptable salt thereof. In some preferred embodiments, the carbon atom to which the Ar group is attached has the D configuration. In certain embodiments, Ar is an unsubstituted or substituted phenyl group. In certain embodiments, Y is hydrogen. In certain preferred embodiments, at least one of $R_6$ and $R_6'$ is selected from the group consisting of an antioxidant moiety, an NMDA antagonist, an NO synthase inhibitor, an iron chelator moiety, a Ca(II) chelator moiety, and a Zn(II) chelator moiety. In certain preferred embodiments, $R_7$ is methyl or mercaptomethyl. In certain preferred embodiments, $R_6$ and $R_6'$ are both hydrogen in certain particularly preferred embodiments, the compound is cyclophenylglycyl-2-(amino-3-mercaptobutanoic acid), more preferably cyclo-D-phenylglycyl-L-[2-(amino-3-mercaptobutanoic acid)]. In a referred embodiment, the compound is cyclo-D-phenylglycyl-(S-Me)-L-cysteine. In some preferred embodiments, Ar is an unsubstituted phenyl group. In certain embodiments, $R_7$ is not hydrogen, methyl or phenyl.

In another embodiment, the invention provides a compound of the formula (Formula IV)

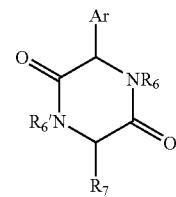

in which Ar represents an unsubstituted or substituted aryl group; $R_7$ is, alkyl, mercaptoalkyl, alkenyl, alkynyl, cycloalkyl, aryl, alkylcarbonyl, arylcarbonyl, alkoxycarbonyl, aryloxycarbonyl, cyano, carboxyl, alkoxycarbonyl, aryloxycarbonyl, or —$(CH_2)_n$—Y, in which n is an integer from 1 to 4 and Y is hydrogen or a heterocyclic moiety selected from the group consisting of thiazolyl, triazolyl, and imidazolyl; $R_6$ is hydrogen or alkyl, alkylcarbonyl, arylcarbonyl, alkoxycarbonyl or aryloxycarbonyl; and $R_6'$ is selected from the group consisting of an antioxidant moiety, an NMDA antagonist, an NO synthase inhibitor, an iron chelator moiety, a Ca(II) chelator moiety, and a Zn(II) chelator moiety; or both $R_6$ and $R_6'$ are selected from the group consisting of an antioxidant moiety, an NMDA antagonist, an NO synthase inhibitor, an iron chelator moiety, a Ca(II) chelator moiety, and a Zn(II) chelator moiety; or a pharmaceutically-acceptable salt thereof. In certain preferred embodiments, $R_6'$ is D-α-aminoadipyl. In certain preferred embodiments, $R_7$ is mercaptomethyl. In certain embodiments, $R_7$ is not hydrogen, methyl or phenyl. In certain preferred embodiments, $R_6'$ further comprises a cleavable linkage. In one embodiment, the compound comprises cyclo-D-phenylglycyl-L-alanine.

As will be appreciated by the skilled artisan, the compounds of the invention include compounds which can have a single pharmacophore (e.g., dioxapiperazines in which the dioxapiperazine moiety is the sole pharmacophore); or β-amino anionic moieties in which the β-amino anionic moiety is responsible for the biochemical activity of the compound. Certain compounds of the invention include two distinct pharmacophores and have a structure represented by A-B, in which A and B are each domains or pharmacophores having biochemical activity (e.g., an anticonvulsant dioxapiperazine moiety having a distinct antioxidant moiety, e.g., $R_6'$) (also referred to herein as a "hybrid" drug). A compound which includes two pharmacophores can be capable of interaction with two or more distinct receptors. Where the compound of the invention includes more than one pharmacophore, the pharmacophores can be linked to each other by a variety of techniques known to the skilled artisan. For example, the pharmacophore represented by $R_6'$ can be covalently bonded to a dioxapiperazine moiety through an amide linkage to a nitrogen of the dioxapiperazine ring. A linkage between two pharmacophores can be selected such that the two pharmacophores are cleaved from each other in vivo (i.e., by the selection of a linkage which is labile in vivo). Examples of such biologically labile linkages are known in the art (see, e.g., R. B. Silverman, "The Organic Chemistry of Drug Design and Drug Action" cited above). Advantageously, such a "hybrid" two-pharmacophore drug can be designed to be transported within the body to reach a site or organ (e.g., the brain), in which one or more pharmacophore moieties exert a biological effect, at which site the hybrid drug can be cleaved to provide two active drug moieties. Some examples of hybrid drugs are set forth hereinabove.

The invention further contemplates the use of prodrugs which are converted in vivo to the therapeutic compounds of the invention (see, e.g., R. B. Silverman, 1992, cited above, Chp. 8). Such prodrugs can be used to alter the biodistribution (e.g., to allow compounds which would not typically cross the blood-brain barrier to cross the blood-brain barrier) or the pharmacokinetics of the therapeutic compound. For example, an anionic group, e.g., a carboxylate or sulfonate, can be esterified, e.g, with a methyl group or a phenyl group, to yield a carboxylate or sulfonate ester. When the carboxylate or sulfonate ester is administered to a subject, the ester is cleaved, enzymatically or non-enzymatically, to reveal the anionic group. Such an ester can be cyclic, e.g., a lactone or sultone, or two or more anionic moieties may be esterified through a linking group. An anionic group can be esterified with moieties (e.g., acyloxymethyl esters) which are cleaved to reveal an intermediate compound which subsequently decomposes to yield the active compound. Alternatively, an anionic moiety can be esterified to a group which is actively transported in vivo, or which is selectively taken up by target organs. The ester can be selected to allow specific targeting of the therapeutic moieties to particular organs. In another embodiment, the prodrug is a reduced form of an anionic group, e.g., a carboxylate or sulfonate, e.g., an alcohol or thiol, which is oxidized in vivo to the therapeutic compound.

Thus, as described above, preferred compounds include pyrimidines, such as substituted uracils, which can be converted in vivo to β-amino anionic compounds. In a preferred embodiment, the compound can be represented by the formula (Formula V):

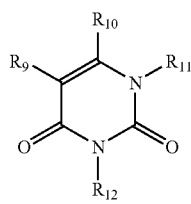

in which $R_9$ and $R_{10}$ are each independently selected from the group consisting of hydrogen, alkyl (including cycloalkyl and aralkyl), alkenyl, alkynyl, aryl, alkoxy, aryloxy, alkylcarbonyl, arylcarbonyl, alkoxycarbonyl, aryloxycarbonyl, amino (including unsubstituted and substituted amino), hydroxy, thiol, alkylthiol, nitro, cyano, halogen, carboxyl, alkoxycarbonyloxy, aryloxycarbonyloxy or aminocarbonyl; or $R_9$ and $R_{10}$, together with the two-carbon unit to which they are attached, are joined to form a carbocyclic or heterocyclic ring having from 4 to 8 members in the ring; and $R_{11}$ is hydrogen, alkyl, alkenyl, alkynyl, cycloalkyl, aryl, alkylcarbonyl, arylcarbonyl, alkoxycarbonyl, or aryloxycarbonyl; or $R_{10}$ and $R_{11}$, together with the carbon atom and nitrogen atom to which they are respectively attached, are joined to form a heterocyclic ring having from 4 to 8 members in the ring; and $R_{12}$ is selected from the group consisting of hydrogen, alkyl, aryl and a carbohydrate (such as a sugar, e.g., ribose or deoxyribose); or a pharmaceutically acceptable salt thereof. In another embodiment, the compound can be represented by the formula (Formula Va):

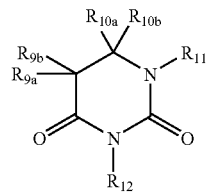

in which $R_{9a}$, $R_{9b}$, $R_{10a}$, $R_{10b}$ are each independently selected from the group consisting of hydrogen, alkyl (including cycloalkyl and aralkyl), alkenyl, alkynyl, aryl, alkoxy, aryloxy, alkylcarbonyl, arylcarbonyl, alkoxycarbonyl, aryloxycarbonyl, amino (including unsubstituted and substituted amino), hydroxy, thiol, alkylthiol, nitro, cyano, halogen, carboxyl, alkoxycarbonyloxy, aryloxycarbonyloxy or aminocarbonyl; or $R_{9a}$ and $R_{9b}$, together with the two-carbon unit to which they are attached, are joined to form a carbocyclic or heterocyclic ring having from 4 to 8 members in the ring; or $R_{10a}$ and $R_{10b}$, together with the two-carbon unit to which they are attached, are joined to form a carbocyclic or heterocyclic ring having from 4 to 8 members in the ring; or one of $R_{9a}$ and $R_{9b}$ is joined with one of $R_{10a}$ and $R_{10b}$ together with the two-carbon unit to which they are attached, to form a carbocyclic or heterocyclic ring having from 4 to 8 members in the ring; $R_{11}$ is hydrogen, alkyl, alkenyl, alkynyl, cycloalkyl, aryl, alkylcarbonyl, arylcarbonyl, alkoxycarbonyl, or aryloxycarbonyl; or one of $R_{10b}$ and $R_{10b}$ is joined with $R_{11}$, together with the carbon atom and nitrogen atom to which they are respectively attached, to form a heterocyclic ring having from 4 to 8 members in the ring; and $R_{12}$ is selected from the group consisting of hydrogen, alkyl, aryl and a carbohydrate (such as a sugar, e.g., ribose or deoxyribose); or a pharmaceutically acceptable salt thereof.

Figure 2:
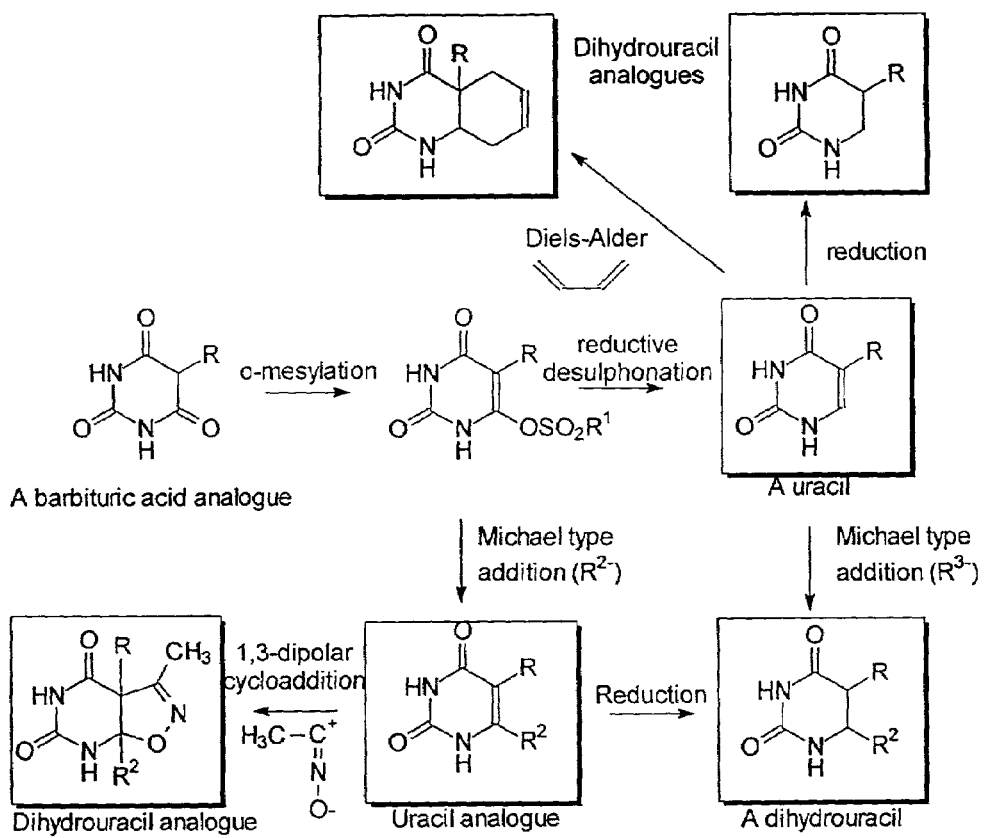
FIG. 2 depicts exemplary synthetic schemes for preparing pyrimidine and dihydropyrimidinecompounds of the invention.

Compounds of Formulas V and Va can be prepared according to a variety of synthetic procedures, some of which are known in the art. Exemplary syntheses are shown in FIG. 2. For example, as shown in FIG. 2, a barbituric acid compound can be modified (e.g., by mesylation, e.g., with mesyl chloride and an amine base) to provide a compound which can be further functionized (e.g., by Michael addition of a suitable nucleophile); or can be reductively desulphonated to provide a dienophile for subsequent Diels-Alder cycloaddition with a suitable dienophile. Reduction of the uracil ring provides dihydrouracil derivatives.

Compounds useful in the present invention may also include carrier or targeting moieties which allow the therapeutic compound to be selectively delivered to a target organ or organs. For example, if delivery of a therapeutic compound to the brain is desired, the compound may include a moiety capable of targeting the compound to the brain, by either active or passive transport (a "targeting moiety"). Illustratively, the carrier molecule may include a redox moiety, as described in, for example, U.S. Pat. Nos. 4,540,564 and 5,389,623, both to Bodor. These patents disclose drugs linked to dihydropyridine moieties which can enter the brain, where they are oxidized to a charged pyridinium species which is trapped in the brain. Thus, drug accumulates in the brain. Other carrier moieties include compounds, such as amino acids or thyroxine, which can be passively or actively transported in vivo. Such a carrier moiety can be metabolically removed in vivo, or can remain intact as part of an active compound. Many targeting moieties are known, and include, for example, asialoglycoproteins (see, e.g. Wu, U.S. Pat. No. 5,166,320) and other ligands which are transported into cells via receptor-mediated endocytosis.

The targeting and prodrug strategies described above can be combined to produce a compound that can be transported as a prodrug to a desired site of action and then unmasked to reveal an active compound.

The invention further provides a kit which includes a container of a compound of the invention and instructions for administering a therapeutically effective amount of the compound to a subject in need thereof such that a convulsive disorder (e.g., epileptogenesis) is inhibited in the subject. The kits of the invention provide convenient means for administering the compounds of the invention. In a particularly preferred embodiment, the kit includes a therapeutically effective amount of the compound, more preferably in unit dosage form.

III. Methods for Preparing β-Amino Anionic Compounds

The invention further provides methods for preparing β-amino anionic compounds.

In one embodiment, the invention comprises a method for preparing a β-amino carboxyl compound represented by the formula (Formula VI):

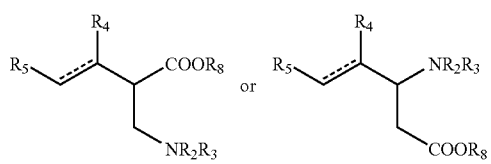

V in which the dashed line represents an optional single/double bond; $R_2$ and $R_3$ are each independently hydrogen, alkyl, alkenyl, alkynyl, cycloalkyl, aryl, alkylcarbonyl, arylcarbonyl, alkoxycarbonyl, or aryloxycarbonyl; or $R_2$ and $R_3$, taken together with the nitrogen to which they are attached, form an unsubstituted or substituted heterocycle having from 3 to 7 atoms in the heterocyclic ring; and $R_4$ and $R_5$ are each independently hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, alkoxycarbonyl, aryloxycarbonyl; or $R_4$ and $R_5$, taken together, form a substituted or unsubstituted carbocyclic or heterocyclic ring having from 5 to 15 atoms (more preferably 5 to 8) in the ring; and $R_8$ is hydrogen, alkyl, aryl, or an organic or inorganic salt-forming cation. The method includes the steps of reacting a compound of formula VI

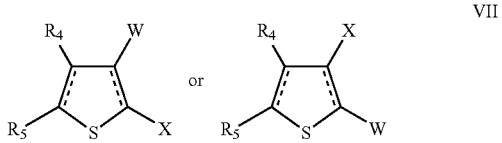

VII in which the dashed lines each represent an optional single/double bond; X is nitro, azido, or $NR_2R_3$, wherein $R_2$ and $R_3$ are defined above; W is —CN or —COOR$_8$; $R_8$ is hydrogen, alkyl, aryl, or an organic or inorganic salt-forming cation; and $R_4$ and $R_5$ are as defined above; under reductive desulfurization conditions such that the β-amino carboxyl or β-amino nitrile compound is formed. In certain preferred embodiments, $R_2$ is alkylcarbonyl, arylcarbonyl, alkoxycarbonyl, or aryloxycarbonyl, and $R_3$ is hydrogen.

Compounds of Formula VII can be prepared according to methods known in the art. For example, the synthesis of aminothiophene carboxylates (i.e., the compound of Formula VI in which W is —COOR$_8$ and $R_8$ is a cation, X is an amino group, and each dashed line is a single bond) has been reported by several methods (see, e.g., Beck, *J. Org. Chem.* (1972) 37:3224; Meth-Cohn, *J. Chem. Res.* (1977) (S)294, (M)3262). Reduction of aminothiophene carboxylates (or aminothiophene nitrites) under reductive desulfurization conditions has now been found to produce β-amino acids in good yield (aminothiophene nitrites also require hydrolysis of the nitrile group, which can be accomplished according to well-known methods; see, e.g., Larock, "Comprehensive Organic Transformations", VCH Publishers (1989), and references cited therein). In a preferred embodiment, the reductive desulfurization conditions comprise reacting the aminothiophene carboxylate with Raney nickel, such that the aminothiophene carboxylate is desulfurized.

In another embodiment, the invention provides a method for preparing a β-amino carboxyl compound represented by formula VIII:

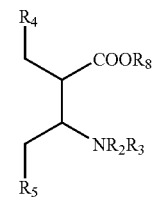

VII in which $R_2$ and $R_3$ are each independently hydrogen, alkyl, alkenyl, alkynyl, cycloalkyl, aryl, alkylcarbonyl, arylcarbonyl, alkoxycarbonyl, or aryloxycarbonyl; or $R_2$ and $R_3$, taken together with the nitrogen to which they are attached, form an unsubstituted or substituted heterocycle having from 3 to 7 atoms in the heterocyclic ring; and $R_4$ and $R_5$ are each independently hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, alkoxycarbonyl, aryloxycarbonyl; or $R_4$ and $R_5$, taken together, form a substituted or unsubstituted carbocyclic or heterocyclic ring having from 5 to 15 atoms (more preferably 5 to 8 atoms) in the ring; and $R_8$ is hydrogen, alkyl, aryl, or an organic or inorganic salt-forming cation. The method includes the steps of reacting a compound of formula IX

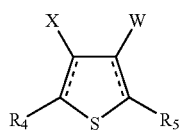

IX in which the dashed lines each represent an optional single bond; X is nitro, azido, or $NR_2R_3$, wherein $R_2$ and $R_3$ are defined above; W is —CN or —COOR$_8$; $R_8$ is hydrogen, alkyl, aryl, or an organic or inorganic salt-forming cation; and $R_4$ and $R_5$ are as defined above; under reductive desulfurization conditions such that the β-amino carboxyl compound of Formula VIII is formed (where W=—CN, the carboxylate will be formed after reductive desulfurization and acidification). In certain preferred embodiments, $R_2$ is alkylcarbonyl, arylcarbonyl, alkoxycarbonyl, or aryloxycarbonyl, and $R_3$ is hydrogen.

Compounds of Formula IX (or esters thereof, which can be hydrolyzed according to known methods to provided compounds of Formula IX) can be prepared according to methods known in the art (see, e.g., U.S. Pat. No. 4,029,647; Henriksen and Autrup, *Acta Chem. Scand.* 26:3342 (1972); Hartke and Peshkar, *Pharm. Zentralhalle* 107:348 (1968)).

The synthetic methods of the invention provide advantages over previously reported syntheses of β-amino acids. For example, the inventive methods provide access to a variety of β-amino acids substituted at either carbon, or both carbons, of the two-carbon backbone; the particular β-amino acid produced is determined by the starting aminothiophene carboxylate, which can be prepared with a variety of substituents. As described in Example 1, infra, the inventive methods provide β-amino acids in good yield, under mild conditions, and in only a small number of steps from commercially-available reagents. Illustrative compounds which have been prepared by this method are presented in Example 1, infra. The methods of the invention thus provide a general, rapid, simple, and high-yielding route to β-amino acids.

In another embodiment, the invention provides a method for preparing a β-aryl-β-alanine compound. In this embodiment, the invention provides a simple, one-pot reaction capable of producing a variety of substituted and unsubstituted β-aryl-β-alanine compounds, often using readily available precursors. This method is an adaptation of previously documented methods (Rodionow, Postouskaja, *J. Am. Chem. Soc.*, 51:841 (1929); Johnson, Livak, *J. Am. Chem. Soc.* 58:299 (1936).) These workers did not synthesize beta-alanines but produced them as side-products. The method used herein is an adaptation to produce beta-alanine analogs. The method includes the steps of reacting an aryl aldehyde with a malonate compound and an ammonium compound, under conditions such that a β-aryl-β-alanine compound is formed. In a preferred embodiment; the aryl aldehyde is a (substituted or unsubstituted) benzaldehyde. In a preferred embodiment, the malonate compound is malonic acid. In a preferred embodiment, the ammonium compound is an ammonium salt of a compound selected from the group consisting of ammonia, primary amines, and secondary amines. A particularly preferred ammonium compound is a salt of ammonia, most preferably ammonium acetate. In a preferred embodiment, the solvent is a polar organic solvent such as ethanol. An exemplary synthesis according to the invention is described in Example 3, infra.

It will be appreciated that β-amino acids, in addition to the anti-epileptogenic properties described herein, are useful for preparing other valuable compounds. For example, the β-lactam structure is present in many commercially-valuable antibiotics, including, for example, penicillins, carbapenems, norcardins, monobactams, and the like. A variety of methods for conversion of β-amino acids to β-lactams have been reported (see, e.g., Wang, W.-B. and Roskamp, E. J., *J. Am. Chem. Soc.* (1993) 115:9417-9420 and references cited therein). Thus, the present invention further provides a method for the synthesis of β-lactams. The method comprises subjecting a compound of Formula VII (or Formula IX) to reductive desulfurization conditions to produce a compound of Formula VI (or I or VIII), followed by cyclization of the compound of Formula VI (or I or VIII) to form a β-lactam. Moreover, β-amino acids have been shown to improve the condition of certain cancer patients (see, e.g., Rougereau, A. et al. *Ann. Gastroenterol. Hepatol. (Paris)* 29 (2): 99-102 (1993). Thus, the present invention provides methods for preparing compounds useful for the treatment of cancer.

IV. Libraries

In another aspect, the invention provides libraries of compounds of Formula IV, Formula VI, or Formula VIII, and methods of preparing such libraries.

The synthesis of combinatorial libraries is well known in the art and has been reviewed (see, e.g., E. M. Gordon et al., *J. Med. Chem.* 37:1385-1401 (1994)). Thus, the subject invention contemplates methods for synthesis of combinatorial libraries of compounds of Formula IV, Formula VI, or Formula VIII. Such libraries can be synthesized according to a variety of methods. For example, a "split-pool" strategy can be implemented to produce a library of compounds. The library of immobilized compounds can then be washed to remove impurities. In certain embodiments, the immobilized compounds can be cleaved from the solid support to yield a compound of Formula IV, VI, or VIII.

In another illustrative method of combinatorial synthesis, a "diversomer library" is created by the method of Hobbs, DeWitt et al. (*Proc. Natl. Acad. Sci. U.S.A.* 90:6909 (1993)). After creation of the library of compounds, purification and workup yields a soluble library of substituted compounds of Formula IV, VI, or VIII.

Other synthesis methods, including the "tea-bag" technique of Houghten (see, e.g., Houghten et al., *Nature* 354: 84-86 (1991)), can also be used to synthesize libraries of compounds according to the subject invention.

Combinatorial libraries can be screened to determine whether any members of the library have a desired activity, and, if so, to identify the active species. Methods of screening combinatorial libraries have been described (see, e.g., Gordon et al., *J Med. Chem.,* op. cit.). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are known in the art (see, e.g., E. M. Gordon et al, *J. Med. Chem.* 37:1385-1401 (1994)).

Combinatorial libraries of compounds can also be synthesized with "tags" to encode the identity of each member of the library (see, e.g., W. C. Still et al., U.S. Pat. No. 5,565,324 and PCT Publication No. WO 94/08051). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels.

In preferred embodiments, the libraries of compounds of the invention contain at least 30 compounds, more preferably at least 100 compounds, and still more preferably at least 500 compounds. In preferred embodiments, the libraries of compounds of the invention contain fewer than $10^9$ compounds, more preferably fewer than $10^8$ compounds, and still more preferably fewer than $10^7$ compounds.

A library of compounds is preferably substantially pure, i.e., substantially free of compounds other than the intended products, e.g., members of the library. In preferred embodiments, the purity of a library produced according to the methods of the invention is at least about 50%, more preferably at least about 70%, still more preferably a, least about 90%, and most preferably at least about 95%.

The libraries of the invention can be prepared according to the methods of the invention. In general, at least one starting material used for synthesis of the libraries of the invention is provided as a variegated population. The term "variegated population", as used herein, refers to a population including at least two different chemical entities, e.g., of different chemical structure. For example, a "variegated population" of compounds of Formula VII would comprise at least two different compounds of Formula VII. Use of a variegated population of linkers to immobilize compounds to the solid support can produce a variety of compounds upon cleavage of the linkers.

Libraries of the invention are useful, e.g., for drug discovery. For example, a library of the invention can be screened (e.g., according to the methods described herein) to determine whether the library includes compounds having a pre-selected activity (e.g., anti-epileptogenic or anticonvulsant activity).

V. Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. In a preferred embodiment, the therapeutic compound is administered orally. The compounds of the invention can be formulated as pharmaceutical compositions for administration to a subject, e.g., a mammal, including a human.

The compounds of the invention are administered to subjects in a biologically compatible form suitable for pharmaceutical administration in vivo. By "biologically compatible form suitable for administration in vivo" is meant a compound to be administered in which any toxic effects are outweighed by the therapeutic effects of the antibody. The term subject is intended to include living organisms in which an immune response can be elicited, e.g., mammals. Examples of subjects include humans, dogs, cats, mice, rats, and transgenic species thereof. Administration of a therapeutically active amount of the therapeutic compositions of the present invention is defined as an amount effective, at dosages and for periods of time necessary to achieve the desired result. For example, a therapeutically active amount of a compound of the invention may vary according to factors such as the disease state, age, sex, and weight of the individual, and the ability of antibody to elicit a desired response in the individual. Dosage regimes may be adjusted to provide the optimum therapeutic response. For example, several divided doses may be administered daily or the dose may be proportionally reduced as indicated by the exigencies of the therapeutic situation.

The active compound may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

A compound of the invention can be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. To administer a compound of the invention by other than parenteral administration, it may be necessary to coat the antibody with, or co-administer the compound with a material to prevent its inactivation. Liposomes include water-in-oil-in-water emulsions as well as conventional liposomes (Strejan et al., (1984) *J. Neuroimmunol* 7:27). The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

When the active compound is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

EXEMPLIFICATION

Example 1

Synthesis of β-Amino Acids: Method A

General Procedures

N-Acetyl Protection via Acetic Anhydride

Acetamidothiophenecarboxylic acid alkyl esters were prepared by refluxing the corresponding amino compound with excess Ac$_2$O (4 equiv.) in anhydrous AcOH for 1 hour. The mixture was poured in cold water and the product was isolated by filtration, washed with water and recrystallized from EtOH.

Synthesis of Raney Nickel Catalyst

A solution of NaOH (320.0 g, 8 mol) in water (1.2 L) was mechanically stirred in a 2.0 L flask. After cooling to 10° C. in an ice-bath, nickel aluminum alloy (250 g) was added in small portions over 90 minutes. The resulting suspension was stirred at room temperature for 1 hour and at 50° C. for an additional 8 hours. The suspension was transferred to a graduated cylinder and the aqueous supernatant was decanted. The resulting slurry was shaken with 2.5 M aqueous NaOH solution (200 mL) then decanted. The nickel catalyst was washed 30 times by suspension in water (150 mL) followed by decanting. The washing was repeated 3 times with absolute EtOH (100 mL) and the resulting Raney nickel was stored under absolute EtOH.

REFERENCES

L. Keefer and G. Lunn. Chem. Rev. 89, 459 (1989).
H. R. Billica and H. Adkins. Org. Synth., Coll. Vol. 3, J. Wiley & Sons, New York, N.Y., 1955, p. 176.

Raney Nickel Reductive Desulfurization

Alkyl acetamidothiophenecarboxylate (20 mmol) and freshly prepared Raney nickel (8 equiv.) were refluxed in EtOH (75 mL) with vigorous stirring for 16 hours. The hot mixture was filtered through diatomaceous earth (Celite) and the nickel residue was washed with hot EtOH (50 mL). The filtrate was concentrated to yield pure N-acetyl-β-alanine alkyl ester as a clear oil, a gum or white crystals.

N-Acetyl and Alkyl Ester Deprotection Via Acidolysis

The doubly protected α- or β-substituted β-alanine was refluxed in 6 M HCl for 5 hours. The solution was evaporated (to remove H$_2$O, HCl, MeOH and AcOH) and the residue was twice dissolved in distilled H$_2$O and concentrated (to remove residual HCl). The product was recrystallized from EtOH to yield the hydrochloride salt as white crystals. Alternatively, the crude product was dissolved in a minimum volume of hot H$_2$O and titrated with NH$_4$OH until the free β-amino acid precipitated. Two volumes of EtOH or MeOH were added to aid the separation of the product and prevent clumping. The mixture was cooled (4° C.) for 24 hours to encourage further precipitation then was filtered. The product was washed with ice cold H$_2$O and EtOH then was recrystallized from MeOH or EtOH to yield pure substituted β-alanine as white crystals.

TLC Analysis

In the experimental procedures that follow, the solvents used for thin-layer chromatographic analysis are abbreviated as follows:

Solvent B: methylene chloride:acetone:acetic acid 100:100:0.5
Solvent I: ethyl acetate:methanol 9:1
Solvent J: chloroform:acetone:water 88:12:15
Solvent K: methanol:acetic acid 5:1
Solvent L: ethanol:acetic acid 50:1

Synthesis of Alkyl Acetamidothiophenecarboxylates

Methyl 3-Acetamidobenzo[b]thiophene-2-carboxylate

Using the procedure described above, methyl 3-aminobenzo[b]thiophene-2-carboxylate (1.8596 g, 8.97 mmol)

was acetylated and purified by EtOH recrystallization to afford pure product as fine white crystals (1.4723 g, 5.91 mmol, 65.9%); mp: 178-180° C.; TLC: $R_f$=0.63 (Solvent I), 0.55 (Solvent J), 0.80 (Solvent L); IR (cm$^{-1}$): 3271 (NH), 3021 (CH), 1716 (ester C=O), 1670 (amide C=O), 746 (=CH); $^1$H nmr (CDCl$_3$): δ 9.46 (br s, 1H), 8.08 (dd, 1H, J=7.0, 2.2 Hz), 7.76 (dd, 1H, J=7.5, 1.0 Hz), 7.48 (d of t, 1H, J=6.9, 1.4 Hz), 7.39 (d of t, 1H, J=7.0, 1.0 Hz), 3.94 (s, 3H), 2.33 (s, 3H).

Methyl 3-Acetamido-6-(trifuoromethyl)benzo[b]thiophene-2-carboxylate

Methyl 3-amino-6-(trifluoromethyl)benzo[b]thiophene-2-carboxylate (1.4944 g, 5.43 mmol) was acetylated and purified by EtOH recrystallization to afford pure product as fluffy, light yellow crystals (1.5261 g, 4.81 mmol, 88.6%); mp: 204-205° C.; TLC: $R_f$=0.72 (Solvent I), 0.78 (Solvent L); IR (cm$^{-1}$): 3274 (NH), 3069 (CH aromatic), 2962 (CH aliphatic), 1720 (ester C=O), 1676 (amino C=O); $^1$H nmr (CDCl$_3$): δ 9.81 (br s, 1H), 8.06 (s, 1H), 7.94 (d, 1H, J=8.7 Hz), 7.51 (dd, 1H, J=8.7, 1.4 Hz), 3.85 (s, 3H), 2.20 (d, 3H, J=4.2 Hz).

Methyl 2-Acetamido-4,5,6,7-tetrahydrobenzo[b]thiophene-3-carboxylate

Methyl 2-amino-4,5,6,7-tetrahydrobenzo[b]thiophene-3-carboxylate (3.0004 g, 14.20 mmol) was acetylated as described above and purified by EtOH recrystallization to afford pure product as light brown crystals (3.3823 g, 13.35 mmol, 94.0%); mp: 103-106° C.; TLC: $R_f$=0.68 (Solvent I), 0.66 (Solvent J), 0.76 (Solvent L); IR (cm$^{-1}$): 3248 (NH), 2932 (CH), 1698 (ester C=O), 1668 (amide C=O); $^1$H nmr (CDCl$_3$): δ 11.22 (br s, 1H), 3.86 (s, 3H), 2.74 (m, 2H), 2.63 (m, 2H), 2.25 (s, 3H), 1.79 (m, 2H), 1.76 (m, 2H).

Methyl 2-Acetamido-6-tert-butyl-4,5,6,7-tetrahydrobenzo[b]thiophene-3-carboxylate Methyl 2-amino-6-tert-butyl-4,5,6,7-tetrahydrobenzo[b]thiophene-3-carboxylate (1.3693 g, 5.12 mmol) was acetylated as described above and purified by EtOH recrystallization to afford pure product as fine white crystals (0.9312 g, 3.01 mmol, 58.8%), mp: 117-118° C.; TLC: $R_f$=0.74 (Solvent I), 0.70 (Solvent J); IR (cm$^{-1}$): 3271 (NH), 2953 (CH), 1674 (C=O); $^1$H nmr (CDCl$_3$): δ 11.20 (br s, 1H), 3.85 (s, 3H), 3.00 (d of m, 1H, J=17.1 Hz), 2.68 (d of m, 1H, J=15.7 Hz), 2.50 (d of m, 1H, J=17.3 Hz), 2.34 (d of m, 1H, J=14.2 Hz), 2.25 (s, 3H), 2.00 (d of m, 1H, J=10.8 Hz), 1.49 (dd, 1H, J=12.0, 5.0 Hz), 1.27 (dd, 1H, J=12.1, 5.1 Hz), 0.93 (s, 9H). (Hazard: Mild sternutator!)

Ethyl 2-Acetamidocyclododeca[b]thiophene-3-carboxylate

Ethyl 2-aminocyclododeca[b]thiophene-3-carboxylate (4.9236 g, 15.91 mmol) was acetylated as described above and purified by EtOH recrystallization to afford pure product as light brown crystals (4.6058 g, 13.10 mmol, 82.3%); mp: 54-74° C.; TLC: $R_f$=0.73 (Solvent I), IR (cm$^{-1}$): 3358 (NH), 2929 (CH), 1710 (ester C=O), 1678 (amide C=O); $^1$H nmr (CDCl$_3$): δ 11.35 (br s, 1H), 4.33 (q, 2H, J=7.3 Hz), 2.75 (t, 2H, J=6.9 Hz), 2.69 (t, 2H, J=7.6 Hz), 2.47 (m, 2H), 2.44 (m, 2H), 2.24 (s, 3H), 1.74 (m, 4H), 1.62 (m, 4H), 1.38 (t, 3H, J=7.2 Hz), 1.30 (m, 4H).

Methyl 2-Acetamido-4,5,6,7-tetrahyro-6-phenylbenzo[b]thiophene-3-carboxylate Methyl 2-amino-4,5,6,7-tetrahydro-6-phenylbenzo[b]thiophene-3-carboxylate (2.5046 g, 8.71 mmol) was acetylated as described above and purified by EtOH recrystallization to afford pure product as a fine off-white powder (2.3763 g, 7.21 mmol, 82.8%); mp: 116-117° C.; TLC: $R_f$=0.79 (Solvent I), 0.78 (Solvent J); IR (cm$^{-1}$): 3255 (NH), 3029 (CH), 2925 (CH), 1686 (ester C=O), 1668 (amide C=O), 703 (=CH); $^1$H nmr (CDCl$_3$): δ 11.25 (br s, 1H), 7.28 (m, 5H), 3.88 (s, 3H), 3.00 (m, 2H), 2.89 (m, 2H), 2.78 (m, 1H), 2.27 (s, 3H), 2.08 (m, 1H), 1.94 (m, 1H).

Methyl 3-Acetamido-5-phenylthiophene-2-carboxylate

Methyl 3-amino-5-phenylthiophene-2-carboxylate (2.5031 g, 10.73 mmol) was acetylated as described above and purified by EtOH recrystallization to afford pure product as white crystals (2.7726 g, 10.07 mmol, 93.8%); mp: 115° C.; TLC: $R_f$=0.70 (Solvent I), 0.70 (Solvent J); IR (cm$^{-1}$): 3319 (NH), 3122 (CH), 2950 (CH), 1715 (ester C=O), 1680 (amide C=O), 765 (=CH); $^1$H nmr (CDCl$_3$): δ 10.18 (br s, 1H), 8.38 (s, 1H), 7.66 (m, 2H), 7.41 (m, 3H), 3.90 (s, 3H), 2.25 (s, 3H).

Methyl 3-Acetamido-5-(4-methoxyphenyl)thiophene-2-carboxylate

Methyl 3-amino-5-(4-methoxyphenyl)thiophene-2-carboxylate (2.5004 g, 9.50 mmol was acetylated and purified by EtOH recrystallization to afford pure product as fine white crystals (2.7173 g, 8.90 mmol, 93.7%); mp: 148-149° C.; TLC: $R_f$=0.68 (Solvent I), 0.65 (Solvent J); IR (cm$^{-1}$): 3303 (NH), 3143 (CH), 2943 (CH), 1705 (ester C=O), 1663 (amide C=O), 817 (=CH); $^1$H nmr (CDCl$_3$): δ 10.19 (br s, 1H), 8.27 (s, 1H), 7.60 (d of m, 2H, J=8.9 Hz), 6.93 (d of m, 2H, J=8.8 Hz), 3.89 (s, 3H), 3.84 (s, 3H), 2.24 (s, 3H).

Methyl 3-Acetamido-5-(4-methylphenyl)thiophene-2-carboxylate

Methyl 3-amino-5-(4-methylphenyl)thiophene-2-carboxylate (1.5098 g, 6.10 mmol) was acetylated as described above and purified by EtOH recrystallization to afford pure product as white fluffy crystals (1.6694 g, 5.77 mmol, 94.6%); mp: 127-129° C.; TLC: $R_f$=0.70 (Solvent I), 0.64 (Solvent J), 0.75 (Solvent K); IR (cm$^{-1}$): 3316 (NH), 2953 (CH), 1710 (ester C=O), 1675 (amide C=O), 812 (=CH); $^1$H nmr (CDCl$_3$): δ 10.18 (br s, 1H), 8.33 (s, 1H), 7.56 (d, 2H, J=8.2 Hz), 7.21 (d, 2H, J=8.0 Hz), 3.89 (s, 3H), 2.38 (s, 3H), 2.24 (s, 3H).

Methyl 3-Acetamido-5-[3-methoxy-4-(4-nitrobenzyloxy)phenyl]thiophene-2-carboxylate Methyl 3-amino-5-[3-methoxy-4-(4-nitrobenzyloxy) phenyl]thiophene-2-carboxylate (1.5174 g, 3.66 mmol) was acetylated as described above and purified by EtOH recrystallization to afford pure product as yellow crystals (1.5487 g, 3.39 mmol, 92.6%); mp: 193-194° C.; TLC: $R_f$=0.68 (Solvent I), 0.65 (Solvent J); IR (cm$^{-1}$): 3326 (NH), 3072 (CH), 2944 (CH), 1705 (ester C=O), 1671 (amide C=O), 836 (=CH); $^1$H nmr (CDCl$_3$): δ 10.19 (br s, 1H), 8.28 (d, 2H, J=2 Hz), 8.23 (s, 1H), 7.62 (d, 2H, J=8.7 Hz), 7.19 (d, 2H, J=5.6 Hz), 6.85 (d, 1H, J=8.9), 5.27 (s, 2H), 3.97 (s, 3H), 3.90 (s, 3H). 2.24 (s, 3H).

Synthesis of N-Acetyl-α-substituted-β-alanine Alkyl Esters

N-Acetyl-α-cyclohexyl-β-alanine Methyl and Ethyl Esters

Methyl 2-acetamido-4,5,6,7-tetrahydrobenzo[b]thiophene-3-carboxylate (0.8125 g, 3.37 mmol) was reductively desulfurized using Raney nickel to yield the title compounds as a light yellow oil (0.6051 g, 2.81 mmol, 83.4%); TLC: $R_f$=0.80 (Solvent I), 0.81 (Solvent L); IR (cm$^{-1}$): 2894 (CH aliphatic), 1738 (ester C=O), 1674 (amide C=O); $^1$H nmr (CDCl$_3$): δ 5.91 (br s, 1H), 4.14 (q, 2H, J=7.1 Hz, minor ethyl ester product), 3.69 (s, 3H), 3.53 (m, 1H), 3.32 (m, 1H), 2.46 (m, 1H), 1.94 (s, 3H), 1.69 (m, 5H), 1.26 (t, 3H, J=7.2 Hz, minor ethyl ester product), 1.14 (m, 6H).

N-Acetyl-α-cyclododecyl-β-alanine Ethyl Ester

Ethyl 2-acetamidocyclododeca[b]thiophene-3-carboxylate (2.3366 g, 6.65 mmol) was reductively desulfurized using Raney nickel to yield the title compound as a yellow oil (2.1314 g, 6.55 mmol, 98.5%); TLC: $R_f$=0.75 (Solvent I), 0.46 (Solvent J); IR (cm$^{-1}$). 3316 (NH), 2903 (CH aliphatic), 1725 (ester C=O), 1661 (amide C=O); $^1$H nmr (DMSO-d6): δ 7.88 (br s, 1H), 4.05 (q, 2H, J=8.1 Hz), 3.59 (m, 2H), 2.45 (m, 1H), 1.74 (s, 3H), 1.50 (m, 1H), 1.28 (m, 22H), 1.15 (t, 3H, J=8.1 Hz).

N-Acetyl-α-(4-tert-butylcyclohexyl)-β-alanine Methyl Ester

Methyl 2-acetamido-6-tert-butyl-4,5,6,7-tetrahydrobenzo[b]thiophene-3-carboxylate (0.8286 g, 2.68 mmol) was reductively desulfurized using Raney nickel to yield the title compound as a sticky white solid (0.7466 g, 2.63 mmol, 98.3%); mp: 73-75° C.; TLC: $R_f$=0.70 (Solvent I), 0.33 (Solvent J); IR (cm$^{-1}$): 3261 (NH), 2943 (CH aliphatic), 1735 (ester C=O), 1648 (amide C=O), $^1$H nmr (CDCl$_3$): δ 5.88 (br s, 1H), 3.69 (s, 3H), 3.53 (m, 1H), 3.41 (m, 1H), 3.34 (m, 1H), 2.44 (m, 1H), 1.94 (s, 3H), 1.77 (m, 2H), 1.63 (m, 1H), 1.50 (m, 1H), 1.27 (t, 1H, J=7.1 Hz), 1.00 (m, 4H), 0.82 (s, 9H).

N-Acetyl-α-(4-phenylcyclohexyl)-β-alanine Methyl Ester

Methyl 2-acetamido-4,5,6,7-tetrahydro-6-phenylbenzo[b]thiophene-3-carboxylate (2.0292 g, 6.16 mmol) underwent Raney nickel reductive desulfurization to yield the title compound as a white solid (1.7908 g, 5.90 mmol, 95.8%); mp: 75-80° C.; TLC: $R_f$=0.58 (Solvent J), 0.79 (Solvent L); IR (cm$^{-1}$): 3259 (NH), 3079 (=CH), 2929 (CH aliphatic), 1730 (ester C=O), 1647 (amide C=O), 698 (=CH); $^1$H nmr (CDCl$_3$): δ 7.29 (m, 3H), 7.19 (m, 2H), 5.94 (br s, 1H), 3.73 (s, 3H), 3.58 (m, 1H), 3.48 (m, 1H), 3.40 (m, 1H), 2.47 (m, 2H), 1.97 (s, 3H), 1.91 (m, 2H), 1.75 (m, 2H), 1.50 (m, 2H), 1.26 (m, 2H).

Synthesis of N-Acetyl-β-substituted-β-alanine Methyl Esters

N-Acetyl-β-phenyl-β-alanine Methyl Ester

Methyl 3-acetamidobenzo[b]thiophene-2-carboxylate (1.3742 g, 5.51 mmol) underwent Raney nickel reductive desulfurization to yield the title compound as a light yellow-brown solid (1.1876 g, 5.37 mmol, 97.4%); mp: 58-61° C.; TLC: $R_f$=0.42 (Solvent I), 0.24 (Solvent J); IR (cm$^{-1}$): 3322 (NH), 3061 (CH aromatic), 2955 (CH aliphatic), 1741 (ester C=O), 1649 (amide C=O); $^1$H nmr (CDCl$_3$): δ 7.30 (m, 5H), 6.62 (br d, 1H, J=6.0 Hz), 5.43 (q, 1H, J=6.0 Hz), 3.62 (s, 3H), 2.89 (dd, 2H, J=8.5, 5.9 Hz), 2.02 (s, 3H).

N-Acetyl-β-(4-trifluoromethylphenyl)-β-alanine Methyl Ester

Methyl 3-acetamido-6-(trifluoromethyl)benzo[b]thiophene-2-carboxylate (0.7014 g, 2.21 mmol) was reductively desulfurized using Raney nickel to yield the title compound as a clear oil (0.5961 g, 2.05 mmol, 92.6%); TLC: $R_f$=0.52 (Solvent I), 0.86 (Solvent L); IR (cm$^{-1}$): 3340 (NH), 1736 (ester C=O), 1654 (amide C=O); $^1$H nmr (DMSO-d6): δ 8.45 (d, 1H, J=8.0 Hz), 7.59 (d, 2H, J=8.3 Hz), 7.49 (d, 2H, J=8. J z), 5.25 (q, 1H, J=7.6, 15 Hz), 3.55 (s, 3H), 2.75 (m, 2H), 1.82 (s, 3H).

N-Acetyl-β-phenethyl-β-alanine Methyl Ester

Methyl 3-acetamido-5-phenylthiophene-2-carboxylate (2.3660 g, 8.59 mmol) underwent Raney nickel reductive desulfurization to yield the title compound as an off-white gum (2.1108 g, 8.47 mmol, 98.6%); TLC: $R_f$=0.68 (Solvent I), 0.65 (Solvent J); IR (cm$^{-1}$): 3475 (NH), 2893 (CH aliphatic), 1735 (ester C=O), 1654 (amide C=O); $^1$H nmr (CDCl$_3$): δ 7.23 (m, 5H), 6.10 (br d, 1H, J=8.8 Hz), 4.30 (t of d, 1H, J=8.9, 5.4 Hz), 3.68 (s, 3H), 2.66 (t, 2H, J=8.2 Hz), 2.57 (dd, 2H, J=4.9, 3.0 Hz), 1.96 (s, 3H), 1.87 (m, 2H).

N-Acetyl-β-(p-methoxyphenethyl]-β-alanine Methyl Ester

Methyl 3-acetamido-5-(4-methoxyphenyl)thiophene-2-carboxylate (1.8100 g, 5.93 mmol) underwent Raney nickel reductive desulfurization to yield the title compound as a yellow oil (1.5544 g, 5.56 mmol, 93.8%); TLC: $R_f$=0.54 (Solvent I), 0.25 (Solvent J); IR (cm$^{-1}$): 3285 (NH), 2944 (CH), 1735 (ester C=O), 1651 (amide C=O), 728 (=CH); $^1$H nmr (CDCl$_3$): δ 7.08 (d, 2H, J=8.5 Hz), 6.81 (d, 2H, J=8.7 Hz), 6.03 (br d, 1H, J=8.7 Hz), 4.27 (m, 1H), 3.77 (s, 3H), 3.67 (s, 3H), 2.59 (t, 2H, J=8.2 Hz), 2.55 (d, 2H, J=8.4 Hz), 1.96 (s, 3H), 1.84 (q, 2H, J=8.2 Hz).

N-Acetyl-β-[2-(4-methylphenyl)ethyl]-β-alanine Methyl Ester

Methyl 3-acetamido-5-(4-methylphenyl)thiophene-2-carboxylate (1.4905 g, 5.15 mmol) was reductively desulfurized using Raney nickel to yield the title compound as a white gum (1.3434 g, 5.10 mmol, 99.1%); mp: 50-51° C.; TLC: $R_f$=0.63 (Solvent I), 0.85 (Solvent L); IR (cm$^1$): 3288 (NH), 2906 (CH aliphatic), 1731 (ester C=O), 1639 (amide C=O), 807 (=CH); $^1$H nmr (CDCl$_3$): δ 7.07 (s, 4H), 6.08 (br d, 1H, J=8.8 Hz), 4.28 (sextet, 1H, J=5.3 Hz), 3.67 (s, 3H), 2.63 (d, 2H, J=8.2 Hz), 2.55 (m, 2H), 2.30 (s, 3H), 1.96 (s, 3H), 1.84 (quintet, 2H, J=7.9 Hz).

N-Acetyl-β-[2-(3-methoxy-4-hydroxyphenyl)ethyl]-β-alanine Methyl Ester

Methyl 3-acetamido-5-[3-methoxy-4-(4-nitrobenzyloxy)phenyl]thiophene-2-carboxylate (1.4481 g, 3.17 mmol) was reductively desulfurized using Raney nickel. The filtered solution was taken up in hot EtOAc then washed with 0.5 N HCl (2×30 mL) and H$_2$O. The organic layer was dried (MgSO$_4$), filtered and concentrated to yield the title compound as a yellow oil (0.5620 g, 1.90 mmol, 60.0%); TLC: R$_f$=0.80 (Solvent L); IR (cm$^{-1}$): 3498 (OH), 2905 (CH aliphatic), 1743 (ester C=O), 1663 (amide C=O), 726 (=CH); $^1$H nmr (CDCl$_3$): δ 6.82 (., 1H, J=7.9 Hz), 6.67 (m, 2H), 6.10 (br d, 1H, J=8.6 Hz), 5.56 (br s, 1H), 4.28 (m, 1H), 3.88 (s, 3H), 3.68 (s, 3H), 2.60 (d, 2H, J=8.4 Hz), 2.55 (t, 2H, J=2.2 Hz), 1.97 (s, 3H), 1.85 (m, 2H).

Synthesis of α-Substituted-β-alanines

α-Cyclohexyl-β-alanine

N-Acetyl-α-cyclohexyl-β-alanine ethyl and methyl esters (2.4499 g, 10.77 mmol) were deprotected to yield the title compound as fine white crystals (0.9573 g, 5.59 mmol, 51.9%); mp: 238-240° C.; TLC: R$_f$=0.75 (Solvent I); IR (cm$^{-1}$): 3300-2700 (OH), 2207, 1635 (carboxylate C=O); $^1$H nmr (TFA-d): δ 4.58 (quintet, 2H), 4.01 (m, 1H), 3.11 (m, 1H), 2.83 (m, 5H), 2.32 (m, 5H).

α-Cyclododecyl-β-alanine Hydrochloride Salt

N-Acetyl-α-cyclododecyl-β-alanine ethyl ester (2.1268 g, 6.83 mmol) was deprotected to yield the title compound as white crystals (0.7322 g, 2.51 mmol, 36.7%); mp: 201-204° C.; TLC: R$_f$=0.79 (Solvent I), 0.80 (Solvent L); IR (cm$^{-1}$): 3400-2700 (OH), 1722 (carboxylate C=O); $^1$H nmr (DMSO-d6): δ 12.72 (br s, 1H), 7.99 (br s, 3H), 2.98 (m, 1H), 2.82 (m, 1H), 2.68 (m, 1H), 1.91 (m, 2H), 1.28 (m, 22H).

α-(4-tert-Butylcyclohexyl)-β-alanine Hydrochloride Salt

N-Acetyl-α-(4-tert-butylcyclohexyl)-β-alanine methyl ester (0.7463 g, 2.63 mmol) was deprotected to yield the title compound as fine white crystals (0.4347 g, 1.65 mmol, 62.7%); mp: 230° C. (dec); TLC: R$_f$=0.91 (Solvent K); IR (cm$^{-1}$): 3400-2700 (OH), 1732 (carboxylate C=O); $^1$H nmr (DMSO-d6): δ 8.02 (br s, 3H), 2.97 (m, 1H), 2.84 (m, 2H), 2.51 (m, 1H), 1.71 (m, 3H), 1.63 (m, 2H), 0.95 (m, 4H), 0.79 (s, 9H).

α-(4-Phenylcyclohexyl)-β-alanine Hydrochloride Salt

N-Acetyl-α-(4-phenylcyclohexyl)-β-alanine methyl ester (1.6699 g, 5.50 mmol) was deprotected to yield the title compound as fine white crystals (0.5235 g, 1.84 mmol, 33.5%); mp: 268° C. (dec); TLC: R$_f$=0.74 (Solvent I), 0.64 (Solvent K); IR (cm$^{-1}$): 3300-2500 (OH), 1701 (carboxylate C=O); $^1$H nmr (DMSO-d6): δ 8.09 (br s, 0.5H), 7.18 (m, 5H), 3.29 (m, 1H), 3.01 (m, 1H), 2.87 (dd, 1H, J=12.8, 4.0 Hz), 2.57 (t, 1H, J=4.5 Hz), 2.45 (m, 1H), 1.75 (m, 5H), 1.29 (m, 3H).

Synthesis of β-Substituted-β-Alanines

β-Phenyl-β-alanine

N-Acetyl-β-phenyl-β-alanine methyl ester (1.1561 g, 5.23 mmol) was deprotected to yield the title compound as fine white crystals (0.5275 g, 3.19 mmol, 61.1%); mp: 220-221° C.; TLC: R$_f$=0.75 (Solvent I); IR (cm$^{-1}$): 3305 (sharp: OH not H-bonded), 2195, 1627 (carboxylate C=O); $^1$H nmr (D$_2$O): δ 7.32 (s, 5H), 4.49 (t, 1H, J=7.9 Hz), 2.71 (d of t, 2H, J=6.5, 1.3 Hz).

β-(4-Trifluoromethylphenyl)-β-alanine Hydrochloride Salt

N-Acetyl-β-(4-trifluoromethylphenyl)-β-alanine methyl ester (0.5850 g, 2.01 mmol) was deprotected to yield the title compound as a white powder (0.5076 g, 1.87 mmol, 93.0%); mp: 203° C. (dec.); TLC: R$_f$=0.60 (Solvent H); IR (cm$^{-1}$): 3500-2900 (OH), 1715 (carboxylate C=O); $^1$H nmr (D$_2$O): δ 7.70 (d, 1H, J=8.1 Hz), 7.54 (d, 2H, J=8.1 Hz), 4.78 (dd, 1H, J=7.0, 7.3 Hz), 3.05 (m, 2H).

β-Phenethyl-β-alanine

N-Acetyl-β-2-phenethyl-β-alanine methyl ester (1.5322 g, 6.15 mmol) was deprotected to yield the title compound as white crystals (0.4709 g, 2.44 mmol, 39.6%); mp: 211-214° C.; TLC: R$_f$=0.37 (Solvent I), 0.74 (Solvent L); IR (cm$^{-1}$): 3496, 3310 (sharp: OH not H-bonded), 3028 (CH), 2932 (CH), 2162, 1663 (carboxylate C=O), 702 (=CH); $^1$H nmr (TFA-d): δ 8.36 (d, 5H, J=15.6 Hz), 4.92 (br s, 1H), 4.14 (br s, 2H), 3.95 (br d, 2H, J=8.0 Hz), 3.32 (br s, 2H).

β-(p-Methoxyphenethyl)-β-alanine

N-Acetyl-β-(p-methoxyphenethyl)-β-alanine methyl ester (1.1244 g, 4.03 mmol) was deprotected and recrystallized from MeOH to give the title compound as off-white crystals (0.2761 g, 1.25 mmol, 31.0%); mp: 180-184° C.; TLC: R$_f$=0.34 (Solvent I), 0.70 (Solvent K); IR (cm$^{-1}$): 3400-2500 (OH), 2171, 1632 (carboxylate C=O); $^1$H nmr (D$_2$O): δ 7.13 (d, 2H, J=8.6 Hz), 6.85 (d, 2H, J=8.5 Hz), 3.69 (s, 3H), 3.37 (m, 1H), 2.57 (t, 2H, J=8.0 Hz), 2.46 (m, 2H), 1.82 (m, 2H).

β-(p-Methylphenethyl)-β-alanine

N-Acetyl-β-[2-(4-methylphenyl)ethyl]-β-alanine methyl ester (1.2884 g, 4.89 mmol) was deprotected to yield the title compound as fluffy white crystals (0.6779 g, 3.27 mmol, 66.9%); mp: 206-207° C.; TLC: R$_f$=0.89 (Solvent K); IR (cm$^{-1}$): 3530, 3280 (sharp: OH not H-bonded), 3017 (CH), 2166, 1706 (carboxylate C=O), 810 (=CH); $^1$H nmr (TFA-d): δ 8.20 (m, 4H), 4.89 (m, 1H), 4.10 (m, 2H), 3.87 (m, 2H), 3.38 (s, 3H), 3.28 (quintet, 2H, J=6.32 Hz).

β-[2-(4-Hydroxy-3-methoxyphenyl)ethyl]-β-alanine Hydrochloride Salt

N-Acetyl-β-[2-(4-hydroxy-3-methoxyphenyl)ethyl]-β-alanine methyl ester (0.5281 g, 1.79 mmol) was deprotected to yield the title compound as a yellow oil (0.4852 g, 1.76 mmol, 98.4%); TLC: R$_f$=0.32 (Solvent I), IR (cm$^{-1}$): 3447 (OH), 1718 (carboxylate C=O); $^1$H nmr (DMSO-d6): 7.79 (br d, 1H, J=8.3 Hz), 6.68 (s, 1H), 6.65 (d, 1H, J=9.5 Hz), 6.49 (d, 1H, J=8.0 Hz), 4.00 (m, 1H), 3.69 (s, 3H), 2.43 (m, 2H), 2.30 (d, 2H, J=6.6 Hz), 1.63 (m, 2H).

Synthesis of 2-Azetidinones

Preparation of N-Substituted 2-Azetidinones from N-Substituted β-Amino Acids $CCl_4$ (1.0 mL, 10 mmol) and triethylamine (TEA) (1.7 mL, 12 mmol) were added to a stirred solution of N-substituted β-amino acid (10 mmol) and $(C_6H_5)_3P$ (1.56 g, 1.2 mmol) in MeCN (100 mL). The reaction mixture was refluxed for 1.5 hours then concentrated in vacuo. The residue was dissolved in $CH_2Cl_2$ (100 mL) and washed with water and brine. The organic layer was dried ($MgSO_4$) and evaporated to dryness. The product was isolated by silica gel flash chromatography using EtOAc/hexane (1:2) as an eluant.

Preparation of N-Silyl 2-Azetidinones from N-Unsubstituted β-Amino Acids

N-Bromosuccinimide (2.14 g, 12 mmol) and TEA (1.7 mL, 12 mmol) were added to a stirred solution of N-unsubstituted β-amino acid (10 mmol) and $(C_6H_5)_3P$ (1.56 g, 1.2; mmol) in MeCN (100 mL). The reaction mixture was stirred at ambient temperature for 10 hours, then concentrated in vacuo. The residue was dissolved in $CH_2Cl_2$ (60 mL), treated with t-butyldimethylsilyl chloride (2.25 g, 15 mmol) and diisopropylamine (2.8 mL, 15 mmol), and stirred at room temperature for 5 hours. The solution was then diluted with $CH_2Cl_2$ (100 mL) and washed with water and brine. The organic layer was dried ($MgSO_4$) and evaporated to dryness. The product was isolated by silica gel flash chromatography using EtOAc/hexane (1:7) as an eluant.

REFERENCE

Sunggak Kim, Phil Ho Lee, and Tai Au Lee. *Synthetic Communications* 18, 247-252 (1988).

Example 2

Figure 3:
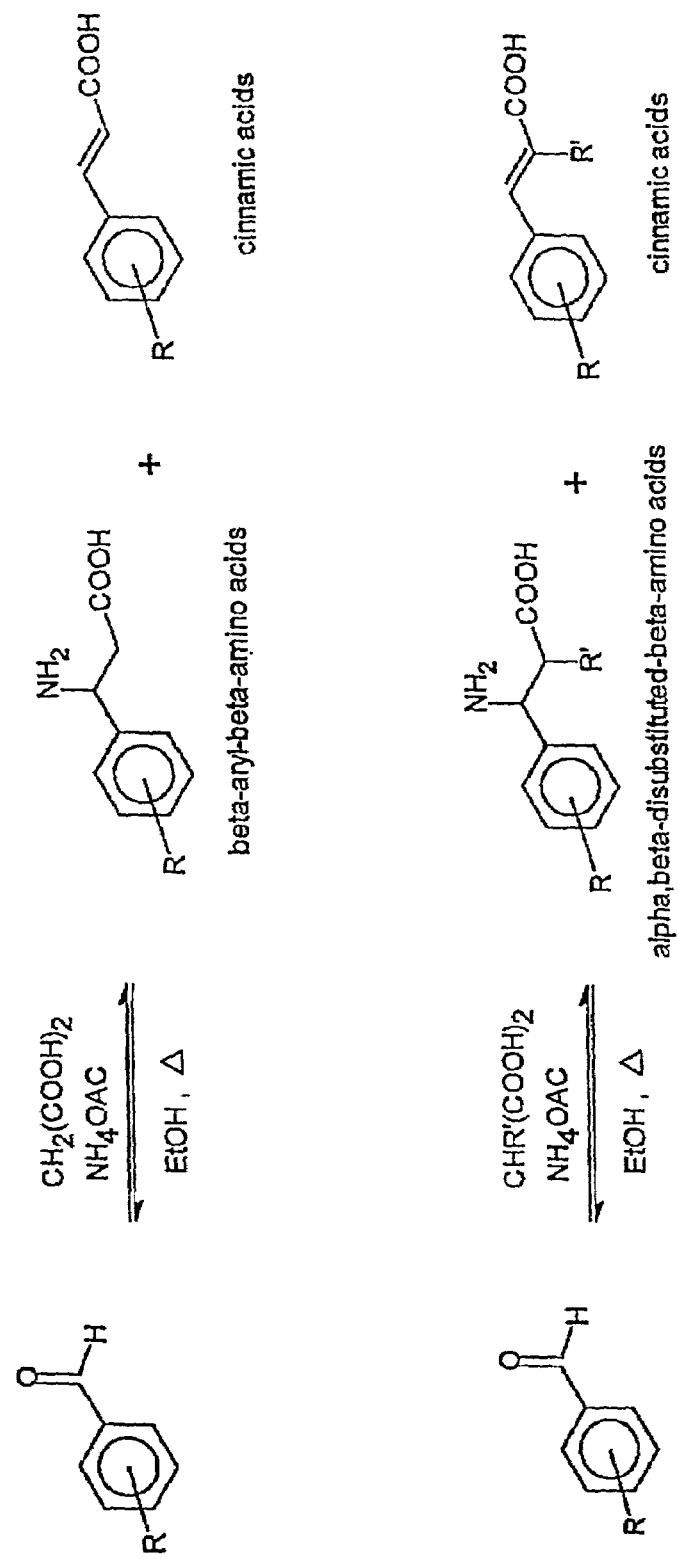
FIG. 3 depicts one embodiment of a synthesis of β-amino acids of the invention.
Figure 4:
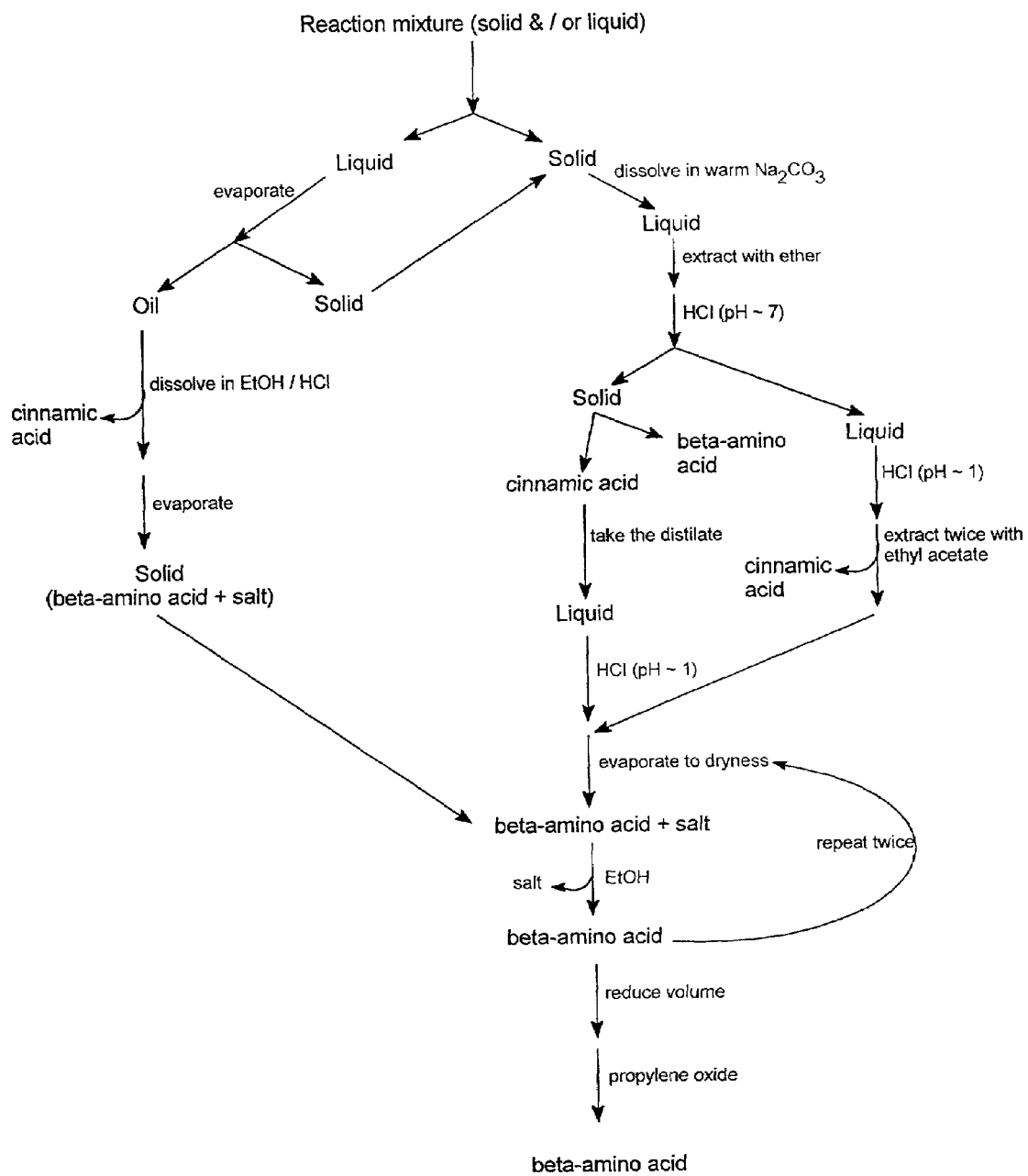
FIG. 4 is a flow chart showing a scheme for purification of β-amino acids.

Synthesis of β-Aryl-β-alanines

β-Aryl-β-alanines were prepared in a one-pot reaction. In brief, to a solution of a substituted benzaldehyde in absolute ethanol was added malonic acid and excess ammonium acetate, and the reaction mixture was heated to reflux. The reaction mixture was cooled to yield a mixture of the β-aryl-β-alanine and (in certain cases) a cinnamic acid derivative. The cinnamic acid (if present) was removed by acid/base extraction of the mixture to yield the β-aryl-β-alanine, often in moderate to good yield. The process is depicted in FIG. 3, and further details of experimental procedures for the synthesis of certain β-aryl-β-alanine compounds are provided infra. A representative purification scheme for purifying the compounds is shown in FIG. 4. Certain compounds prepared as described herein are set forth in Table 1, infra. Yield data are represented in two colums, the second being identical to that in Table 2, infra.

TABLE 1

β-aryl-β-alanines prepared from benzaldehydes.

| Compound RCH(NH$_2$)CH$_2$COOH | Yield (%) | Yield (%) (from Table 2) |
|---|---|---|
| R = | | |
| 4-Fluorophenyl | 68.5% | 61.5% |
| 4-Phenoxyphenyl | 39.7% | 68.1% |

TABLE 1-continued

β-aryl-β-alanines prepared from benzaldehydes.

| Compound RCH(NH$_2$)CH$_2$COOH | Yield (%) | Yield (%) (from Table 2) |
|---|---|---|
| 3-Methylphenyl | 56.4% | 56.4% |
| 3-Methyl-4-methoxyphenyl | 52.7% | 52.7% |
| 3-(3,4-dichlorophenoxy)phenyl | 32.6% | 42.6% |
| 2-Methylphenyl | 19.0% | 19.0% |
| 3-(4-chlorophenoxy)phenyl | 23.2% | 33.2% |
| 2,5-Dimethyl-4-methoxyphenyl | 12.6% | 22.6% |
| 4-Trifluoromethoxyphenyl | 15.2% | 46.2% |
| 2-Chlorophenyl | 21.7% | 27.7% |
| 2-Fluoro-3-trifluoromethylphenyl | 5.5% | 15.5% |
| 3-Bromo-4-methoxyphenyl | 23.8% | 43.8% |
| 4-Bromophenyl | 34.2% | 69.2% |
| Phenyl | 61.1% | 67.1% |
| 4-Methylphenyl | 51% | 51.0% |
| 4-Chlorophenyl | 12% | 65.0% |
| 4-Acetamidophenyl | 23% | 23.0% |
| 2,5-Dimethoxyphenyl | 22% | 22.0% |
| 4-Diethylaminophenyl | | |
| 3-Methylphenyl | 45.4% | 45.8% |
| 2-Hydroxy-3-methoxyphenyl | 11% | 17.2% |
| 4-Phenylphenyl | 40.2% | 40.2% |
| 3,4-Dibenzyloxyphenyl | 36.2% | 36.2% |
| 3-[(3-Trifluoromethyl)phenyloxy]phenyl | 29.7% | 39.7% |

Selected compounds synthesized by this method are shown in Table 1, supra. Representative syntheses of certain of these compounds, and additional compounds of the invention, are set forth below.

β-substituted-β-amino-acids were prepared by refluxing the corresponding benzaldehyde derivatives with excess ammonium acetate (~2 equiv.), and malonic acid (1 equiv.) in absolute ethanol until the reaction has completed (determined by TLC and NMR). Cinnamic acid derivative was produced as a side product. The reaction mixtures were then workup with standard procedures, e.g., as described in FIG. 4.

β-3(3,4-dichlorophenoxy)phenyl-β-alanine Hydrochloride Salt

Using the procedure described above, 3-(3,4-dichlorophenoxy)benzaldehyde (10 g, 37.4 mmol), ammonium acetate (3.8437 g, 49.8 mmol) and malonic acid (3.8923 g, 37.4 mmol) were refluxed (slow) in absolute ethanol (30 mL) for 5 hours. β-3(3,4-dichlorophenoxy)phenyl-β-alanine as white solid was then filtered and washed twice with 10 mL of absolute ethanol. Subsequently, addition of 10 mL 3N HCl was added to this β-3(3,4-dichlorophenoxy)phenyl-β-alanine to afford the β-3(3,4-dichlorophenoxy)phenyl-β-alanine hydrochloride salt (4.44 g, 12.2 mmol, 32.6%); MP: 164-165° C.; IR (KBr): 3193, 1609 cm$^{-1}$; $R_F$=0.55 (solvent 24), 0.72 (solvent 25); $^1$H NMR (D$_2$O/K$_2$CO$_3$): δ 7.31-6.57 (m, 7H), 4.03 (t, J=7.29 Hz, 1H)? 2.4-2.29 (m, 2H). Anal. Calcd for C$_{15}$H$_4$Cl$_3$NO$_3$: C, 49.68; H, 3.89; N, 3.86. Found: C, 49.34; H, 3.87; N, 3.93.

β-4-bromophenyl-β-alanine

4-Bromobenzaldehyde (10 g, 54 mmol), ammonium acetate (8.663 g, 112.4 mmol) and malonic acid (5.6762 g, 54.5 mmol) were refluxed (slow) in absolute ethanol (45 mL) for 150 hours. White solid was filtered and dissolved into a warm (70° C.) solution of 50 mL of Na$_2$CO$_3$ and 50 mL of H₂O. This solution was then extracted with 100 mL of diethyl ether three times. The aqueous layer was further acidified to pH 7 to produce white solid β-4-bromophenyl-β-alanine (4.5140 g, 18.49 mmol, 34.2%); MP: 234° C.; IR (KBr): 3061, 1594 cm$^{-1}$; TLC: $R_F$=0.35 (solvent 24), 0.32 (solvent 25); $^1$H NMR (D₂O/K₂CO₃): δ 7.42-7.38 (m, 2H), 7.17-7.14 (m, 2H), 4.11-4.07 (t, J=7.25 Hz, 1H), 2.48-2.36 (m, 2H). Anal. Calcd for C₉H₁₀BrNO₂: C, 44.29; H, 4.13; N, 5.74. Found: C, 44.35; H, 3.93; N, 5.70.

β-4-fluorophenyl-β-alanine

4-Fluorobenzaldehyde (10 g, 80 mmol), ammonium acetate (8.2487 g, 107 mmol) and malonic acid (8.3285 g, 80 mmol) were refluxed (slow) in absolute ethanol (60 mL) for 48 hours. White solid was filtered and purified by ethanol recrystallization to afford β-4-fluorophenyl-β-alanine (10.04 g, 54.8 mmol, 68.5%); MP: 216-217° C.; IR (KBr): 3160, 1606 cm$^{-1}$; TLC: $R_F$=0.41 (solvent 24), 0.42 (solvent 25); $^1$H NMR (D₂O/K₂CO₃): δ 7.28-7.19 (m, 2H), 7.03-6.91 (m, 2H), 4.10 (t, J=7.39 Hz, 1H), 2.54-2.34 (m, 2H). Anal. Calcd for C₉H₁₀FNO₂.5/3H₂O: C, 50.70; H, 6.30; N, 6.57. Found: C, 50.34; H, 6.39; N, 6.30.

β-2,5-dimethoxyphenyl-β-alanine 2,5-dimethoxybenzaldehyde (4.1437 g, 25 mmol), ammonium acetate (3.1200 g, 40.47 mmol) and malonic acid (3.1244 g, 30.02 mmol) were refluxed (slow) in absolute ethanol (60 mL) for 6 hours. White solid was filtered and purified by methanol recrystallization to afford β-2,5-dimethoxyphenyl-β-alanine (1.239 g, 5.5 mmol, 22.0%); MP: 206-208° C.; IR (KBr): 2944, 1630 cm$^{-1}$; TLC: $R_F$=0.29 (solvent 21), 0.66 (solvent 23); $^1$H NMR (200 MHz, D₂O/K₂CO₃): δ 6.9-6.7 (m, 3H), 4.3 (t, J=7.89 Hz, 1H), 3.7-3.6 (m, 6H) 2.55-2.2 (m, 2H). Anal. Calcd for C₁₁H₁₅NO₄.6/5H₂O: C, 53.52; H, 7.10; N, 5.67. Found: C, 53.85; H, 6.45; N, 5.56.

β-3-bromo-4-methoxyphenyl-β-alanine

3-Bromo-4-methoxylbenzaldehyde (9.9835 g, 46.42 mmol), ammonium acetate (7.2984 g, 94.69 mmol) and malonic acid (4.9124 g, 47.21 mmol) were refluxed (slow) in absolute ethanol (110 mL) for 281 hours. White solid was filtered and dissolved into a warm (70° C.) solution of 50 mL of Na₂CO₃ and 50 mL of H₂O. This solution was then extracted with 100 mL of diethyl ether three times. The aqueous layer was further acidified to pH 1 and extracted with 100 mL of ethyl acetate twice. Subsequently the aqueous layer was evaporated to dryness and 30 mL of absolute ethanol was then added to the white residue, stirred for 15 min, and filtered. The same procedure was then repeated twice. The final mixture was filtered, and the filtrate was evaporated to dryness. Propylene oxide (9.75 mL, 139.3 mmol) was added to the ethanol portion. The solution was stirred and warmed up to 50° C. to produce β-3-bromo-4-methoxyphenyl-β-alanine (3.0284 g, 11.05 mmol, 23.8%); MP: 213° C.; IR (KBr): 2945, 1604 cm$^{-1}$; TLC: $R_F$=0.26 (solvent 24), 0.28 (solvent 25); $^1$H nmr (D₂O/K₂CO₃): δ 7.42 (s, 1H), 7.18-7.14 (d d, 1H), 6.91-6.87 (d, 1H), 4.05-3.98 (t, 1H), 3.71 (s, 1H), 2.47-2.30 (m, 2H). Anal. Calcd for C₁₀H₁₂BrNO₃1/5H₂O: C, 43.25; H, 4.50; N, 5.04. Found: C, 43.16; H, 4.24; N, 4.94.

Additional compounds as synthesized generally in accordance with the previous paragraphs, and analytical data there for are provided below in Table 2.

TABLE 2

β-aryl-β-alanines prepared from benzaldehydes.

| Compound | Yield | m.p. (° C.) | TLC ($R_f$) | NMR (PPM) |
|---|---|---|---|---|
| B5P91<br>C₉H₁₁NO₂  MW = 165.20 | 67.1% | 220-221 | 21: 0.54<br>23: 0.60 | 7.35-7.2 (s, 5H)<br>4.45 (t, 1H, 7.3 Hz)<br>2.8-2.1 (m, 2H)<br>solubility: ~10 mg/ml saline |
| B6P165<br>C₁₀H₁₄NO₂Cl  MW = 215.68 | 51% | 208-210 | 21: 0.57<br>23: 0.56 | 7.2-7.1 (M, 4H)<br>4.17-4.09(t, 1H, 7.4 Hz)<br>2.39-2.46 (m, 2H)<br>solubility: ~10 mg/ml saline |

TABLE 2-continued

β-aryl-β-alanines prepared from benzaldehydes.

| Compound | Yield | m.p. (° C.) | TLC (R$_f$) | NMR (PPM) |
|---|---|---|---|---|
| B6P169  (4-Cl-C$_6$H$_4$-CH(NH$_3$Cl)-CH$_2$-COOH) <br> C$_9$H$_{11}$NO$_2$Cl$_2$  MW = 236.10 | 65% | 186-189 | 21: 0.54 <br> 23: 0.54 | 7.3-7.17 (s, 4H) <br> 4.07-4.17 (t, 7H, 7.2 Hz) <br> 2.45-2.55 (dt, 4.5 Hz, 3.5 Hz) <br> solubility: ~10 mg/ml saline |
| B7P16  (4-CH$_3$CONH-C$_6$H$_4$-CH(NH$_3$Cl)-CH$_2$-COOH) <br> C$_{11}$H$_{14}$N$_2$O$_3$  MW = 222.24 | 23% | 221-222 | 21: 0.32 <br> 23: 0.60 | 7.2-7.3 (s, 4H) <br> 4.05-4.15 (t, 1H, 7.4 Hz) <br> 2.4-2.5 (dt, 4.9 Hz, 2.5 Hz) <br> solubility: ~10 mg/ml saline |
| B8P22  (2,5-diOMe-C$_6$H$_3$-CH(NH$_2$)-CH$_2$-COOH) <br> C$_{11}$H$_{15}$NO$_4$  MW = 225.23 | 22% | 206-208 | 21: 0.29 <br> 23: 0.66 | 6.9-6.7 (m, 3H) <br> 4.3 (t, 1H, 7.89 Hz) <br> 3.7-3.6 (m, 6H) <br> 2.55-2.2 (m, 2H) |
| B8P25  (4-(Et)$_2$N-C$_6$H$_4$-CH(NH$_3$Cl)-CH$_2$-COOH) <br> C$_{13}$H$_{21}$N$_2$O$_2$Cl  MW = 272.77 |  | 228 | 21: 0.298 <br> 23: 0.48 <br> 24: 0.48 | 6.7-6.8 (d, 2H, 8.71 Hz) <br> 7.1-7.2 (d, 2H, 8.72 Hz) <br> 4.0-4.1 (t, 1H, 7.28 Hz) <br> 3.0-3.1 (M, 4H) <br> 2.3-2.4 (M, 2H) <br> 0.8-0.9 (M, 6H) |
| B8P58  (3-Me-C$_6$H$_4$-CH(NH$_2$)-CH$_2$-COOH) <br> C$_{10}$H$_{13}$NO$_2$  MW = 179.22 | 45.8% | 226-227 | 24: 0.297 <br> 25: 0.324 | 6.9-7.2 (M, 4H) <br> 4.0-4.1 (t, 1H, 7.37 Hz) <br> 2.4 (M, 2H) <br> 2.2 (M, 3H) |
| B8P13  (3-MeO-2-OH-C$_6$H$_3$-CH(NH$_2$)-CH$_2$-COOH) <br> C$_{10}$H$_{13}$NO$_4$  MW = 211.22 | 17.2% | 200-201 | 24: 0.324 <br> 25: 0.324 | 6.6-6.8 (M, 3H) <br> 4.4-4.5 (t, 1H, 7.30 Hz) <br> 3.6 (s, 3H) <br> 2.5 (dd, 2H, 7.25 Hz) |

TABLE 2-continued

β-aryl-β-alanines prepared from benzaldehydes.

| Compound | Yield | m.p. (° C.) | TLC (R$_f$) | NMR (PPM) |
|---|---|---|---|---|
| B8P85 (4-F-C$_6$H$_4$-CH(NH$_2$)-CH$_2$-COOH) C$_9$H$_{10}$FNO$_2$  MW = 183.17 | 61.5% | 216-217 | 24: 0.41<br>25: 0.42 | 7.28-7.19 (m, 2H)<br>7.03-6.91 (m, 2H)<br>4.10 (t, 1H, 7.29 Hz)s<br>2.54-2.34 (m, 2H) |
| B8P79 (4-PhO-C$_6$H$_4$-CH(NH$_2$)-CH$_2$-COOH) C$_{15}$H$_{15}$NO$_3$  MW = 257.29 | 68.1% | 214-215 | 24: 0.65<br>25: 0.43 | 7.33-7.23 (m, }<br>7.09-7.03 (m, } 9H<br>6.96-6.89 (m, }<br>4.08-4.16 (t, 1H, 7.23 Hz)<br>2.46-2.42 (dd, 2H, 7.12 Hz, 2.386 Hz) |
| B8P91 (3-(4-CH$_3$-C$_6$H$_4$-O)-C$_6$H$_4$-CH(NH$_2$)-CH$_2$-COOH) C$_{16}$H$_{17}$NO$_3$  MW = 271.32 | 56.4% | 205-208 | 24: 0.53<br>25: 0.58 | 7.28-6.77 (m, 8H)<br>4.08 (t, 1H, 7.30 Hz)<br>2.42-2.38 (d, 2H, 7.29 Hz)<br>2.189 (s, 3H) |
| B8P89 (3-CH$_3$-4-CH$_3$O-C$_6$H$_3$-CH(NH$_2$)-CH$_2$-COOH) C$_{11}$H$_{15}$NO$_3$  MW = 209.31 | 52.7% | 237-240 | 24: 0.20<br>25: 0.46 | 7.07-7.1 (m, 2H)<br>6.82-6.88 (m, 1H)<br>4.05-4.12 (t, 1H, 7.286 Hz)<br>3.708 (s, 3H)<br>2.39-2.46 (m, 2H)<br>2.064 (s, 3H) |
| B8P81 (3-(3,4-Cl$_2$-C$_6$H$_3$-O)-C$_6$H$_4$-CH(NH$_3$Cl)-CH$_2$-COOH) C$_{15}$H$_{14}$Cl$_3$NO$_3$  MW = 364.14 | 42.6% | 164-165 | 24: 0.55<br>25: 0.72 | 7.31-6.57 (m, 7H)<br>4.03 (t, 1H, 6.38 Hz)<br>2.4-2.29 (m, 2H) |
| B8P74 (2-CH$_3$-C$_6$H$_4$-CH(NH$_2$)-CH$_2$-COOH) C$_{10}$H$_{13}$NO$_2$  MW = 179.22 | 19.0% | 219 | 24: 0.487<br>25: 0.308 | 7.30-7.27 (m, 1H)<br>7.20-7.05 (m, 3H)<br>4.1-4.0 (t, 1H, 7.35 Hz)<br>2.44-2.39 (dd, 2H, 6.56 Hz, 1.93 Hz)<br>2.26-2.24 (s, 3H) |

TABLE 2-continued

β-aryl-β-alanines prepared from benzaldehydes.

| Compound | Yield | m.p. (° C.) | TLC ($R_f$) | NMR (PPM) |
|---|---|---|---|---|
| B8P95<br>4-Cl-C$_6$H$_4$-O-C$_6$H$_4$-CH(NH$_2$)-CH$_2$-COOH<br>$C_{15}H_{14}ClNO_3$  MW = 291.73 | 33.2% | 202-203 | 24: 0.52<br>25: 0.488 | 7.29-7.22 (m, }<br>7.06-7.03 (d, } 8H<br>6.91-6.81 (m, }<br>4.08 (t, 1H, 7.29 Hz)<br>2.42-2.38 (d, 1H, 7.25 Hz) |
| B8P93<br>2,5-(CH$_3$)$_2$-4-OCH$_3$-C$_6$H$_2$-CH(NH$_2$)-CH$_2$-COOH<br>$C_{12}H_{17}NO_3$  MW = 223.27 | 22.6% | 228 | 24: 0.58<br>25: 0.62 | 7.07 (s, 1H)<br>6.71 (s, 1H)<br>4.38 (t, 1H, 6.89 Hz)<br>3.69 (s, 3H)<br>2.39-2.36 (d, 2H, 7.24 Hz)<br>2.20 (s, 3H)<br>2.03 (s, 3H) |
| B8P101<br>4-F$_3$CO-C$_6$H$_4$-CH(NH$_2$)-CH$_2$-COOH<br>$C_{10}H_{10}F_3NO_3$  MW = 249.19 | 46.2% | 222-223 | 24: 0.64<br>25: 0.268 | 7.34-7.30 (d, 2H, 8.71 Hz)<br>7.20-7.16 (d, 2H, 8.102 Hz)<br>4.18-4.11 (t, 1H, 7.23 Hz)<br>2.46-2.41 (dd, 2h, 7.426 Hz, 2.914 Hz) |
| B8P68<br>2-Cl-C$_6$H$_4$-CH(NH$_2$)-CH$_2$-COOH<br>$C_9H_{10}ClNO_2$  MW = 199.64 | 27.7% | 219 | 24: 0.38<br>25: 0.61 | 7.38-7.12 (m, 4H)<br>5.05 (t, 1H, 6.4 Hz)<br>2.62-2.27 (m, 2H) |
| B8P83<br>3-F$_3$C-2-F-C$_6$H$_3$-CH(NH$_2$)-CH$_2$-COOH<br>$C_{10}H_9F_4NO_2$  MW = 251.18 | 15.5% | 206 | 24: 0.486<br>25: 0359 | 7.54-7.50 (m, 2H)<br>7.24-7.20 (t, 1H, 7.912 Hz)<br>4.50-4.37 (t, 1H, 7.3 Hz)<br>2.53-2.49 (d, 2H, 7.38 Hz) |
| B8P135<br>3-Br-4-CH$_3$O-C$_6$H$_3$-CH(NH$_2$)-CH$_2$-COOH<br>$C_{10}H_{12}BrNO_3$  MW = 274.11 | 43.8% | 213 | 24: 0.256<br>25: 0.275 | 7.42 (s, 1H)<br>7.18-7.14 (d of d, 1H)<br>6.87-6.91 (d, 1H)<br>4.05-3.98 (t, 2H)<br>3.71 (s, 3H)<br>2.47-2.30 (m, 2H) |

TABLE 2-continued

β-aryl-β-alanines prepared from benzaldehydes.

| Compound | Yield | m.p. (° C.) | TLC ($R_f$) | NMR (PPM) |
|---|---|---|---|---|
| B8P163 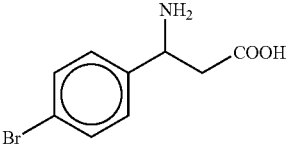 $C_9H_{10}BrNO_2$ MW = 244.09 | 69.2% | 234 | 24: 0.35<br>25: 0.32 | 7.38-7.42 (m, 2H)<br>7.14-7.17 (m, 2H)<br>4.07-4.11 (t, 1H, 7.25 Hz)<br>2.36-2.48 (m, 2H) |
| B8P159 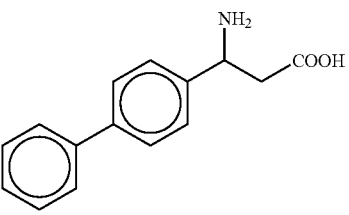 $C_{15}H_{15}NO_2$ MW = 241.29 | 40.2 | 244 | 24: 0.27<br>25: 0.47 | 7.19-7.46 (m, 9H)<br>4.13-4.18 (t, 1H, 6.7 Hz)<br>2.39-2.43 (d, 2H, 7.2 Hz) |
| B8P147 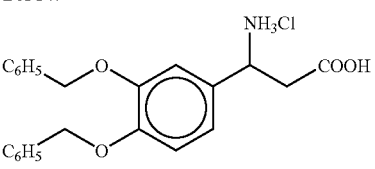 $C_{23}H_{24}ClNO_4$ MW = 413.90 | 36.2 | 198-200 | 24: 0.41<br>25: 0.43 | 7.35-7.21 (m, 10H)<br>7.07-6.92 (m, 3H)<br>5.07 (s, 4H)<br>4.41-4.37 (t, 1H, 8.86)<br>2.89-2.83 (m, 2H) |
| B8P155 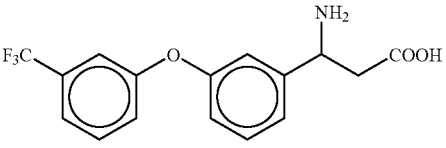 $C_{16}H_{14}F_3NO_3$ MW = 413.90 | 39.7 | 192-194 | 24: 0.49<br>25: 0.44 | 7.53-7.37 (m, 3H)<br>7.23-7.13 (m, 4H)<br>7.02-6.97 (m, 1H)<br>4.49-4.45 (t, 1H, 7.1 Hz)<br>2.64-2.61 (m, 2H) |

TLC Analysis

In the experimental procedures above, the solvents used for thin layer chromatographic analysis are abbreviated as follow:

Solvent 21: acetonitrile:acetic acid:water 8:1:1
Solvent 23: methanol:acetic acid 7:1
Solvent 24: n-butanol:acetic acid:water 4:1:1
Solvent 25: methanol:chloroform:acetic acid 7:7:1:

Additional analytical and biological data for β-aryl-β-alanines, β-phenethyl-β-alanines, α-cyclohexyl-β-alanines, and α-substituted-β-alanines (and certain esters and amides thereof) as well as 4'-substituted N-acetyl-α-piperidinyl-β-alanine, are shown in Table 3.

TABLE 3

A. Analytical and Biological Activity Data for β-Aryl-β-Alanines and Precursors

| Compound | R₁ | R₂ | R₃ | Yield[a] (%) | m.p. (°C.) | TLC[b] (R_f) | IR (cm⁻¹) ν | H nmr[c] δ | Biological Activity[d] |
|---|---|---|---|---|---|---|---|---|---|
| B5P65 | CH₃ | Ac | H | 97.4 | 58-61 | 0.42 (I) | 3322 (NH), 1741 (C=O), 1649 (C=O) | | NA |
| B6P140 | CH₃ | Ac | p-F₃C | 87.1 | oil | 0.52 (I) | 3340 (NH), 1736 (C=O), 1654 (C=O) | [e]7.30 (m, 5H), 6.62 (br d, 1H, J=6.0 Hz), 5.43 (q, 1H, J=6.0 Hz), 3.62 (s, 3H), 2.89 (dd, 2H, J=5.9, 8.5 Hz), 2.02 (s, 3H) [f]8.45 (d, 1H, J=8.0 Hz), 7.59 (d, 2H, J=8.3 Hz), 7.49 (d, 2H, J=8.1 Hz), 5.25 (q, 1H, J=7.6, 15 Hz), 3.55 (s, 3H), 2.75 (m, 2H), 1.82 (s, 3H) | NA |
| B5P91 | H | H | H | 61.1[g] | 220-221 | 0.75 (I) | 3305 (OH), 1627 (C=O) | [h]7.32 (s, 5H), 4.49 (t, 1H, J=7.9 Hz), 2.71 (d of t, 2H, J=6.5, 1.3 Hz) | Inactive |
| B6P141 | H | H.HCl | p-F₃C | 93.0 | 203 (dec.) | 0.60 (H) | 3500-299 (OH), 1715 (C=O) | [f]7.70 (d, 1H, J=8.1 Hz), 7.54 (d, 2H, J=8.1 Hz), 4.78 (dd, 1H, J=7.0, 7.3 Hz), 3.05 (m, 2H) | Active |

[a]EtOH, H₂O or a mix used for recrystallization;
[b]Solvent systems:
I: EtOAc:MeOH 9:1;
H: MeOH:AcOH 5:1;
[c]¹H nmr solvents:
[e]CDCl₃,
[f]DMSO-d6,
[h]D₂O;
[d]Using pilocarpine, compound is active in rat at 100 mg/kg, or inactive;
[g]48% [150].

B. Analytical and Biological Activity Data for Aryl Substituted β-Phenethyl-β-alanine and Precursors TABLE 3-continued

| ID | | | R3 | % | form | Rf | IR | NMR | |
|---|---|---|---|---|---|---|---|---|---|
| B5P69 | CH₃ | Ac | p-CH₃O | 93.8 | oil | 0.54 (I) | 3285 (NH), 1735 (C=O), 1651 (C=O) | ᵃ7.08 (d, 2H, J=8.5 Hz), 6.81 (d, 2H, J=8.7 Hz), 6.03 (br d, 1H, J=8.7 Hz), 4.27 (m, 1H), 3.77 (s, 3H), 3.67 (s, 3H), 2.59 (t, 2H, J=8.2 Hz), 2.55 (d, 2H, J=8.4 Hz), 1.96 (s, 3H), 1.84 (q, 2H, J=8.2 Hz) | NA |
| B5P73 | CH₃ | Ac | H | 98.6 | Gum | 0.68 (I) | 3475 (NH), 1735 (C=O), 1654 (C=O) | ᵃ7.23 (m, 5H), 6.10 (br d, 1H, J=8.8 Hz), 4.30 (t of d, 1H, J=8.9, 5.4 Hz), 3.68 (s, 3H), 2.66 (t, 2H, J=8.2 Hz), 2.57 (dd, 2H, J=4.9, 3.0 Hz), 1.96 (s, 3H), 1.87 (m, 2H) | NA |
| B6P89 | CH₃ | Ac | p-CH₃ | 99.1 | 50–51 | 0.63 (I) | 3288 (NH), 1731 (C=O), 1639 (C=O) | ᵃ7.07 (s, 4H), 6.08 (br d, 1H, J=8.8 Hz), 4.28 (sextet, 1H, J=5.3 Hz), 3.67 (s, 3H), 2.63 (d, 2H, J=8.2 Hz), 2.55 (m, 2H), 2.30 (s, 3H), 1.96 (s, 3H), 1.84 (quintet, 2H, J=7.9 Hz) | NA |
| B6P101 | CH₃ | Ac | m-NEt | 100 | Oil | 0.62 (I) | 3440 (NH), 1731 (C=O), 1633 (C=O) | ᵃ7.11 (t, 1H, J=7.5 Hz), 6.48 (br t, 3H), 6.05 (br d, 1H, J=8.4 Hz), 4.31 (m, 1H), 3.67 (s, 3H), 3.33 (q, 2H, J=7.0 Hz), 2.59 (t, 2H, J=8.4 Hz), 2.56 (d, 2H, J=4.4 Hz), 2.39 (br s, 1H), 1.94 (s, 3H), 1.87 (m, 2H), 1.14 (t, 3H, J=7.0 Hz) | NA |
| B6P113 | CH₃ | Ac | m,p-OCH₂O | 97.5 | Oil | 0.53 (I) | 1729 (C=O), 1654 (C=O) | ᵃ7.01 (d, 1H, J=8.4 Hz), 6.75 (d, 1H, J=8.4 Hz), 6.65 (m, 1H), 6.1 (m, 1H), 5.90 (s, 0.5H), 4.25 (m, 1H), 3.68 (s, 3H), 2.57 (m, 2H), 2.53 (m, 2H), 1.97 (m, 1H), 1.27 (m, 2H), 1.51 (impurity), 1.24 (impurity) | NA |
| B6P119 | CH₃ | Ac | p-OH m-CH₃O | 60.0 | Oil | 0.80 (L) | 3498 (OH), 1743 (C=O), 1663 (C=O) | ᵃ6.82 (d, 1H, H=7.9 Hz), 6.67 (m, 2H), 6.10 (br d, 1H, J=8.6 Hz), 5.56 (br s, 1H), 4.28 (m, 1H), 3.88 (s, 3H), 3.68 (s, 3H), 2.60 (d, 2H, J=8.4 Hz), 2.55 (t, 2H, J=2.2 Hz), 1.97 (s, 3H), 1.85 (m, 2H) | NA |
| B5P81 | H | H | p-CH₃O | 31.0 | gum | 0.34 (I) 0.70 (K) | 3400–2500 (OH), 1632 (C=O) | ᵃ7.13 (d, 2H, J=8.6 Hz), 6.85 (d, 2H, J=8.5 Hz), 3.69 (s, 3H), 3.37 (m, 1H), 2.57 (t, 2H, J=8.0 Hz), 2.46 (m, 2H), 1.82 (m, 2H) | 0 |

| Compound | R₁ | R₂ | R₃ | Yield % | mp | Rf | IR | ¹H NMR | Activity |
|---|---|---|---|---|---|---|---|---|---|
| B5P95 | H | H | H | 39.6 | 211–214[g] | 0.37 (I) | 3310 (OH), 1663 (C=O) | [k]8.36 (d, 5H, J=15.6 Hz), 4.92 (br s, 1H), 4.14 (br s, 2H), 3.95 (br d, 2H, J=8.0 Hz), 3.32 (br s, 2H)[i] | +1 |
| B5P111 | H | H | p-CH₃ | 66.9 | 206–207 | 0.89 (K) | 3280 (OH), 1706 (C=O) | [k]8.20 (m, 4H), 4.89 (m, 1H), 4.10 (m, 2H), 3.87 (m, 2H), 3.38 (s, 3H), 3.28 (quintet, 2H, J=6.3 Hz) | Inactive |
| B6P145 | H | H | p-OH m-CH₃O | 98.4 | oil | 0.32 (I) | 3447 (OH), 1718 (C=O) | [j]7.79 (br d, 1H, J=8.3 Hz), 6.68 (s, 1H), 6.65 (d, 1H, J=8.3 Hz), 6.49 (d, 1H, J=8.0 Hz), 4.00 (m, 1H), 3.69 (s, 3H), 2.43 (m, 2H), 2.30 (d, 2H, J=6.6 Hz), 1.76 (impurity), 1.63 (m, 2H) | +1 |

[a]EtOH, H₂O or a mix used for recrystallization, where possible;
[b]Solvent systems:
I: EtOAc:MeOH 9:1;
L: EtOH:AcOH 50:1;
K: MeOH:AcOH 5:1;
[c]¹H nmr solvents:
[e]CDCl₃,
[f]D₂O,
[h]TFA-d,
[i]DMSO-d6;
[d]Using pilocarpine, compound is active in rat at 100 mg/kg, or inactive;
[g]226–228° C. (dec.) [194];
[j]¹H nmr in D₂O [144].

C. Analytical and Biological Activity Data for 4′-Substituted α-Cyclohexyl-β-alanine and Precursors

| Compound | R₁ | R₂ | R₃ | Yield % | mp | Rf | IR | ¹H NMR | Activity |
|---|---|---|---|---|---|---|---|---|---|
| B6P77 | Ac | CH₃ | H | 93.5 | Oil | 0.80 (I) | 1738 (C=O), 1674 (C=O) | [e]5.91 (br s, 1H), 4.14 (q, J=7.1 Hz)**, 3.69 (s, 3H), 3.53 (m, 1H), 3.32 (m, 1H), 2.46 (m, 1H), 1.94 (s, 3H), 1.69 (m, 5H), 1.26 (t, J=7.2 Hz)**, 1.14 (m, 6H) | NA |
| B6P81 | Ac | CH₃ | Ph | 95.8 | 75–80 | 0.79 (L) | 3259 (NH), 1730 (C=O), 1647 (C=O) | [e]7.29 (m, 5H), 7.19 (m, 2H), 5.94 (br s, 1H), 3.73 (s, 3H), 3.58 (m, 1H), 3.48 (m, 1H), 3.40 (m, 1H), 2.47 (m, 2H), 1.97 (s, 3H), 1.91 | NA |

TABLE 3-continued

| Compound | R₁ | R₂ | R₃ | Yield (%) | m.p. (° C.) | TLC[a] (R_f) | IR (cm⁻¹) ν | H nmr (CDCl₃) | Biological Activity |
|---|---|---|---|---|---|---|---|---|---|
| B6P109 | Ac | CH₃ | C(CH₃)₃ | 98.3 | 73–75 | 0.70 (I) | 3261 (NH), 1735 (C=O), 1648 (C=O) | (m, 2H), 1.75 (m, 2H), 1.50 (m, 2H), 1.26 (m, 2H) [c]5.88 (br s, 1H), 3.69 (s, 3H), 3.53 (m, 1H), 3.41 (m, 1H), 3.34 (m, 1H), 2.44 (m, 1H), 1.94 (s, 3H), 1.77 (m, 2H), 1.63 (m, 1H), 1.50 (m, 1H), 1.27 (t, 1H, J=7.1 Hz), 1.00 (m, 4H), 0.82 (s, 9H) | NA |
| B5P107 | H·HCl | H | Ph | 33.5 | 268–270 | 0.74 (I) | 3300–2500 (OH), 1701 (C=O) | [f]8.09 (br s, 0.5 H), 7.18 (m, 5H), 3.29 (m, 1H), 3.01 (m, 1H), 2.87 (dd, 1H, J=4.0, 12.8 Hz), 2.57 (t, 1H, J=4.5 Hz), 2.45 (m, 1H), 1.75 (m, 5H), 1.29 (m, 3H) | +3 activity |
| B5P119 | H | H | H | 51.9 | 238–240 | 0.75 (I) | 3300–2700 (OH), 1635 (C=O) | [g]4.58 (quintet, 2H), 4.01 (m, 1H), 3.11 (m, 1H), 2.83 (m, 5H), 2.32 (m, 5H) | +1 |
| B5P127 | H·HCl | H | C(CH₃)₃ | 62.7 | 230 (dec) | 0.91 (K) | 3400–2700 (OH), 1732 (C=O) | [f]8.02 (br s, 3H), 2.97 (m, 1H), 2.84 (m, 3H), 2.51 (m, 1H), 1.71 (m, 3H), 1.63 (m, 2H), 0.95 (m, 4H), 0.79 (s, 9H) | 0 |

**Partial Et-13 Me exchange has occurred due to solvolysis.
**EtOH, H₂O or a mix used for recrystallizations;
[a]Solvent systems:
I: EtOAc:MeOH 9:1;
L:EtOH:AcOH 50:1;
K: MeOH:AcOH 5:1;
[c]¹H nmr solvents:
[c]CDCl₃;
[f]DMSO-d6,
[g]TFA-d;
[d]Using pilocarpine, compound is active in rat at 100 mg/kg, or inactive.

D. Analytical and Biological Activity Data for 4-Substituted N-Acetyl-α-piperidinyl-β-alanine methyl ester TABLE 3-continued

| Compound | R₁ | R₂ | R₃ | R₄ | m.p. (°C.) | Yield[a] (%) | TLC[a] (R_f) | IR (cm⁻¹) ν | H nmr (DMSO d6) | Biological Activity |
|---|---|---|---|---|---|---|---|---|---|---|
| B6P105 | Ac | CH₃ | CO₂Et | | gum | 96.8 | 0.65 (I) | 1743 (C=O), 1708 (C=O), 1673 (C=O) | 5.92 (br s, 1H), 4.16 (q, J=6.6Hz)**, 4.10 (q, 2H, H=7.1 Hz), 3.70 (s, 3H), 3.52 (m, 1H), 3.41 (m, 1H), 2.69 (m, 2H), 2.51 (m, 1H), 2.01 (m, 2H), 1.95 (s, 3H), 1.79 (m, 1H), 1.71 (d of m, 2H), 1.55 (d of m, 2H), 1.30 (t, J=6.6 Hz)**, 1.23 (t, 3H, J=7.0 Hz) | NA |

**Partial Et—Me exchange has occured due to solvolysis.
[a]Solvent system:
I: EtOAc:MeOH 9:1.

E. Analytical and Biological Activity Data for N-Acetyl-α-substituted-β-alanine methyl ester and α-Substituted-β-alanine

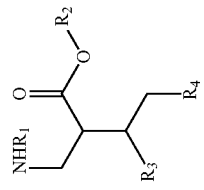

| Compound | R₁ | R₂ | R₃ | R₄ | m.p. (°C.) | Yield[a] (%) | TLC[a] (R_f) | IR (cm⁻¹) ν | H nmr (DMSO d6) | Biological Activity |
|---|---|---|---|---|---|---|---|---|---|---|
| B6P85 | Ac | CH₃ | | —CH₂CH₂CH₂— | Oil | NA | 0.54 (I) | 1720 (C=O), 1660 (C=O) | 7.78 (br s, 1H), 4.03 (q, J=7.0 Hz)**, 3.57 (s, 3H), 3.30 (m, 1H), 3.09 (m, 2H), 2.35 (m, 2H), 1.87 (m, 2H), 1.76 (s, 3H), 1.49 (m, 5H), 1.17 (t, J=7.0 Hz)** | NA |
| B6P93 | Ac | CH₃ | Et | CH₃ | Oil | 83.4 | 0.75 (I) | 3189 (NH), 1723 (C=O), 1665 (C=O) | 7.80 (br m, 1H), 3.58 (s, 3H), 3.26 (m, 1H), 3.04 (m, 1H), 2.59 (m, 1H), 1.76 (s, 3H), 1.5–1.1 (m, 5H), 0.9–0.7 (m, 6H) | NA |
| B6P97 | Ac | CH₃ | H | Bu | Gum | 99.6 | 0.53 (I) | 1739 (C=O), 1658 (C=O) | 7.54 (br d, 1H, J=8.1 Hz), 3.70 (s, 3H), 2.51 (br d, 2H, J=6.3 Hz), 1.94 (s, 3H), 1.51 (br m, 2H), 1.33 (br m, 8H), 0.94 (m, 3H) | NA |
| B6P117 | Ac | Et | | —CH₂(CH₂)₃CH₂— | Oil | 79.7 | 0.77 (I) | 3216 (NH), 1727 (C=O), 1666 (C=O) | d5.89 (br s, 1H), 4.16 (d of q, 2H, J=7.0, 4.0 Hz), 3.62 (d of q, 1H, J=3.7, 13.5 Hz), 3.25 (d of q, 1H, | NA |

TABLE 3-continued

| | | | | | | | |
|---|---|---|---|---|---|---|---|
| B6P133 | Ac | Et | —CH$_2$(CH$_2$)$_8$CH$_2$— | Oil | 98.5 | 0.75 (I) | 3316 (NH), 1725 (C=O), 1661 (C=O) | J=5.2, 13.5 Hz), 2.52 (d of q, 1H, J=3.7, 9.5 Hz), 1.94 (s, 3H), 1.7–1.3 (br m, 11H), 1.27 (t, 3H, J=7.0 Hz) | NA |
| B5P131 | H.HCl | H | —CH$_2$(CH$_2$)$_8$CH$_2$— | 201–204 | 36.7 | 0.79 (I) | 3400-2700 (OH), 1722 (C=O) | 7.88 (br s, 1H), 4.05 (q, 2H, J=8.1 Hz), 3.59 (m, 2H), 2.45 (m, 1H), 1.74 (s, 3H), 1.50 (m, 1H), 1.28 (m, 22H), 1.15 (t, 3H, J=8.1 Hz) 12.72 (br s, 1H), 7.99 (br s, 3H), 2.98 (m, 1H), 2.82 (m, 1H), 2.68 (m, 1H), 1.91 (m, 1H), 1.28 (m, 24H) | Inactive |

**Partial Et—Me exchange has occurred due to solvolysis.

[a]Yield of last synthetic step;
[b]Solvent system I: EtOAc:MeOH 9:1;
[c]Using pilocarpine, compound is active in rat at 100 mg/kg, or inactive;
[d]$^1$H nmr solvent: CDCl$_3$.

Example 4

The "spontaneous recurrent seizures" (SRS) model of epilepsy was used to evaluate candidate compounds in a model for Phase 1 epileptogenesis (see, e.g., Mello, E. et al., *Epilepsia* (1993) 34:985; Cavalheiro, J. et al., *Epilepsia* (1991) 32:778). In the SRS model, an adult male Sprague-Dawley rat (c. 260 g) is given pilocarpine by injection (380 mg/kg i.p.). Within 25 minutes, the animal enters status epilepticus, which typically lasts for 15-20 hours (although about 10% of animals die at this stage). The rat is allowed to spontaneously recover and is given food and water ad lib. and maintained on a 12 hour/12 hour light/dusk cycle. Rats are usually studied in groups of four. Beginning on about day 13-15, the rats develop spontaneous recurrent seizures, which occur at the rate of about 4-5 per week. The rats are videotaped 24 hours per day, and the videotapes are reviewed for behavioral seizures (including head nodding, forelimb clonus, and rearing), which are counted. The animals are watched for three months, permitting evaluation of a sufficient number of seizures. An experimental compound for evaluation can be administered at either of two times: Time 1, on Day 1, after the cessation of status epilepticus but before the onset of SRS; or Time 2, on Day 30, when the rats have been experiencing SRS for about two weeks. Administration of the candidate compound at Time 1 permits evaluation for anti-epileptogenic properties (ability to prevent the onset of seizures); administration of compounds at Time 2 permits evaluation of drugs as anti-ictogenics with the ability to suppress established seizures.

As a reference, the standard anticonvulsant phenytoin was administered (20 mg/kg/day i.v. for 10 day) at either Time 1 or Time 2. As expected, phenytoin was ineffective in preventing the onset of seizures when administered at Time 1, but was 75% effective at decreasing seizure frequency by 50% or more when administered at Time 2.

In contrast, β-alanine and an analog (α-(4-tert-butylcyclohexyl)-alanine (see Example 1) were administered at a comparable dosage (20 mg/kg/day i.v. for 10 days) at either Time 1 or Time 2 using the same protocal outlined above. At Time 1, each of these compounds was 75% effective in decreasing seizures by at least 50%; at Time 2, each compound was 50% effective in decreasing seizures by at least 50%.

The compounds of the invention listed in Tables 2 and 3, supra, were tested for biological activity per Example 6. The following compounds were found to have at least weak activity: β-p-methylphenyl-β-alanine hydrochloride, β-2-hydroxy-3-methoxyphenyl-β-alanine, β-3-methyl-4-methoxyphenyl-β-alanine (slight), β-3-(3,4-dichlorophenoxy) phenyl-β-alanine hydrochloride (moderate), β-2,5-dimethyl-4-methoxyphenyl-β-alanine, β-p-(trifluoromethoxy)phenyl-β-alanine, and β-2-fluoro-3-(trifluoromethyl)phenyl-β-alanine (moderate).

Thus, β-amino acids show activity both as anti-epileptogenic compounds and as anti-ictogenic compounds.

Example 5

Dioxapiperazine compounds were synthesized according to standard methods and and characterized by NMR, FAB-MS, melting point, and HPLC. The crystal structures of several compounds were determined.

An exemplary procedure is as follows:

Boc-L-alanine (1.5 g, 0.008 mol) was dissolved in 60 ml ethyl acetate, to which 2.4 g 2-ethoxycarbonyl-1,2-dihydroquinoline (EEDQ) (0.010 mol, 1.2 equiv.) was added. The solution was stirred for 5 minutes, after which D-phenylglycine methyl ester HCl (1.5 g, 0.003 mol) was added. Stirring was continued for 24 hours, and then the solution was washed with 3×25 mL 10% (w/w) $KHSO_4$ (aq), 25 mL saturated NaCl solution, 3×25 saturated sodium bicarbonate solution, and 25 mL satuarated NaCl solution. The organic layer was dried over magnesium sulfate and evaporated to yield a clear oil. The oil was dissolved in 20 ml formic acid and stirred for two hours at room temperature. The acid was removed by evaporation and the oil was suspended in a mixture of 50 mL 2-butanol and 25 mL toluene. The mixture was refluxed for 24 hours, cooled over two hours with stirring, and the solvent reduced to above one-fourth the original volume in vacuo. The solid was allowed to crystallize. Cyclo-D-phenylglycine-L-alanine was obtained as a white solid (1.1 g, 0.005 mol, 68% yield) with a melting range of 260-265° C.

Example 6

Selected compounds were dissolved in 0.9% NaCl or suspended in a mixture of 30% polyethylene glycol 400 and 70% water, and tested in an animal model. Briefly, the compounds were administered intraperitoneally or or orally to carsworth Farms #1 mice (in a volume of 0.01 ml/g of body weight) or Sprague-Dawley rats (in a volume of 0.004 ml/g body weight). Times on peak effect and peak neurologic deficit were determined before the anticonvulsant tests were administered.

The maximal electroshock seizure test (MES), corneal electrodes primed with a drop of electrolyte solution (0.9% NaCl) were applied to the eyes of the animal and an electrical stimulus (50 mA for mice, 150 mA for rats; 60 Hz) was delivered for 0.2 second at the time of the peak effect of the test compound. The animals were restrained by hand and released at the moment of stimulation in order to permit observation of the seizure. Abolition of hind-leg tonic-extensor component (hind-leg tonic extension does not exceed a 90° angle to the plane of the body) indicated that the compound prevented MES-induced seizure spread.

In the subcutaneous pentylenetetrazol threshold test (sc-Met), the convulsant dose (CD97) of pentylenetetrazol (85 mg/kg in rats) was injected at the time of peak effect of the test compound. The animals were isolated and observed for 30 minutes to see whether seizures occurred. Absence of clonic spasms persisting for at least five seconds indicated that the compound could elevate the pentylenetetrazol induced seizure threshold.

Acute anti-convulsant drug-induced toxicity in lab animals is usually characterized by some type of neurologic abnormality. In mice, these abnormalities can be detected by the rotorod ataxia test, which is somewhat less useful in rats. In the rotorod ataxia test, neurologic deficit is indicated by the inability of the animal to maintain equilibrium for at least one minute on a knurled rod rotating at 6 rpm. Rats were examined by the positional sense test: one hind leg is gently lowered over the edge of a table, whereupon the normal animal will lift the leg back to a normal position. Inability to return the leg to normal position indicates a neurologi deficit.

Example 7

Testing of the compounds was performed in 12 mice at doses of 30, 100, 300 mg/kg (4 mice each) 30 minutes and four hours after the test compounds was administered. The results are shown in Table 4.

TABLE 4

Selected Dioxapiperazine Compounds and Testing data.

| Compound | Activity: 300 mg/kg | Activity: 100 mg/kg | Activity: 30 mg/kg |
|---|---|---|---|
| c/D-Peg-L-Ala | 4 | 3 | 2 |
| c/L-Peg-L-Ala | 0 | 0 | NA |
| c/D-Peg-Gly | 2 | 1 | 0 |
| c/D-Peg-L-Lys | 1 | 0 | NA |
| c/D-Peg-D-Lys | 0 | 0 | NA |
| c/D-Peg-L-Ornithine (Orn) | 0 | 0 | NA |
| c/D-Peg-D-Orn | 0 | 0 | NA |
| c/D-Peg-L-diaminobutyric acid | 0 | 0 | NA |
| c/D-Peg-L-diaminopropionic acid | 0 | 0 | NA |
| c/D-Peg-L-Met | 1 | 0 | NA |
| c/D-Peg-D-Met | 0 | 0 | NA |
| c/D-Peg-L-(S-methyl)-L-cysteine | 4 | 3 | 2 |
| c/D-Peg-L-(S-benzyl)-L-cysteine | 0 | 0 | NA |
| c/D-Peg-L-Arg | 0 | 0 | NA |
| c/D-Peg-L-HomoArg | 0 | 0 | NA |
| c/D-Peg-N-guanidine-L-homoArg | 0 | 0 | NA |
| c/D-(p-OH)-Peg-L-Ala | 0 | 0 | NA |
| c/D-(p-OH)-Peg-L-Lys | 0 | 0 | NA | c = cyclo
Peg = phenylglycine
Activity on scale of 0 (inactive) to 4.

As seen in Table 4, c/D-phenylglycine-L-alanine and c/D-phenylglycine-(S-Me)-L-cysteine exhibited strong anticonvulsive activity in this animal model system, while several other dioxapiperazines showed weaker anti-convulsive activity.

Certain other diozapiperazines were also synthesized and tested. Of these compounds, only c/L-alanine-D-leucine was found to be active.

Those skilled in the art will recognize, or be able to ascertain using no more than routine experimentation, numerous equivalents to the specific procedures described herein. Such equivalents are considered to be within the scope of this invention and are covered by the following claims.

The contents of all publications cited herein are hereby incorporated by reference.

Other embodiments are within the following claims.

What is claimed is:

1. A method of inhibiting epileptogenesis, comprising administering to a subject in need thereof an effective amount of a substituted β-amino anionic compound, comprising an amino group, an anionic group, and a two-carbon spacer unit, wherein
said anionic group is a carboxylate; and
said amino group is —NR$^a$R$^b$, wherein R$^a$ and R$^b$ are each independently hydrogen, alkyl, alkenyl, alkynyl, cycloalkyl, aryl, alkylcarbonyl, arylcarbonyl, alkoxycarbonyl, or aryloxycarbonyl; or R$^a$ and R$^b$, taken together with the nitrogen to which they are attached, form an unsubstituted or substituted heterocycle having from 3 to 7 atoms in the heterocyclic ring, wherein said amino group and said anionic group are separated by said two-carbon spacer unit;
wherein said two-carbon spacer unit may be substituted with a substituent selected from the group consisting of halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, azido, heterocyclyl, aromatic, and heteroaromatic moieties;
or a pharmaceutically acceptable salt or ester thereof, such that epileptogenesis is inhibited.

2. A method for treating a convulsive disorder, comprising administering to a subject in need thereof an effective amount of a substituted β-amino anionic compound, comprising an amino group, an anionic group, and a two-carbon spacer unit, wherein
said anionic group is a carboxylate; and
said amino group is —NR$^a$R$^b$, wherein R$^a$ and R$^b$ are each independently hydrogen, alkyl, alkenyl, alkynyl, cycloalkyl, aryl, alkylcarbonyl, arylcarbonyl, alkoxycarbonyl, or aryloxycarbonyl; or R$^a$ and R$^b$, taken together with the nitrogen to which they are attached, form an unsubstituted or substituted heterocycle having from 3 to 7 atoms in the heterocyclic ring, wherein said amino group and said anionic group are separated by said two-carbon spacer unit;
wherein said two-carbon spacer unit may be substituted with a substituent selected from the group consisting of halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, azido, heterocyclyl, aromatic, and heteroaromatic moieties;
or a pharmaceutically acceptable salt or ester thereof, such that said convulsive disorder is treated.

3. A method for treating a convulsive disorder, comprising administering to a subject in need thereof an effective amount of a substituted β-amino anionic compound, comprising an amino group, an anionic group, and a two-carbon spacer unit, wherein
said anionic group is a carboxylate; and
said amino group is —NR$^a$R$^b$, wherein R$^a$ and R$^b$ are each independently hydrogen, alkyl, alkenyl, alkynyl, cycloalkyl, aryl, alkylcarbonyl, arylcarbonyl, alkoxycarbonyl, or aryloxycarbonyl; or R$^a$ and R$^b$, taken together with the nitrogen to which they are attached, form an unsubstituted or substituted heterocycle having from 3 to 7 atoms in the heterocyclic ring, wherein said amino group and said anionic group are separated by said two-carbon spacer unit;
wherein said two-carbon spacer unit may be substituted with a substituent selected from the group consisting of halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, azido, heterocyclyl, aromatic, and heteroaromatic moieties;

or a pharmaceutically acceptable salt or ester thereof, such that epileptogenesis is inhibited.

4. The method of any one of claims 1, 2, or 3, wherein $R^a$ and $R^b$ are each independently hydrogen, alkyl, alkylcarbonyl; or $R^a$ and $R^b$, taken together with the nitrogen to which they are attached, form an unsubstituted or substituted heterocycle having from 3 to 7 atoms in the heterocyclic ring.

5. The method of any one of claims 1, 2, or 3, wherein said two-carbon spacer unit is substituted with an amino substituent, wherein said amino substituent is an alkyl amino, dialkylamino, arylamino, diarylamino, or alkylarylamino moiety.

6. The method of any one of claims 1, 2, or 3, wherein said two-carbon spacer unit is substituted with an acylamino substituent, wherein said acylamino substituent is an alkylcarbonylamino, arylcarbonylamino, carbamoyl, or ureido moiety.

7. The method of any one of claims 1, 2, or 3, wherein said two-carbon spacer unit is substituted with a substituent selected from the group consisting of aromatic and alkoxy moieties; and $R^a$ and $R^b$ are each independently hydrogen, alkyl, or alkylcarbonyl; or $R^a$ and $R^b$, taken together with the nitrogen to which they are attached, form an unsubstituted or substituted heterocycle having from 3 to 7 atoms in the heterocyclic ring.

8. The method of any one of claims 1, 2, or 3, wherein said two-carbon spacer unit is substituted with a substituent selected from the group consisting of substituted aromatic moieties.

9. The method of claim 8, wherein said substituted aromatic or substituted aryloxy moiety is substituted with a substituent selected from the group consisting of halogens, hydroxyl, alkoxyl, amino, alkylamino, dialkylamino, arylamino, alkylcarbonylamino, and aromatic moieties.

10. The method of any one of claims 1, 2, or 3, wherein said two-carbon spacer unit is substituted with a substituent selected from the group consisting of carboxylate, alkylcarbonyl, alkoxycarbonyl, aminocarbonyl, alkylthiocarbonyl, phosphonato, phosphinato, acylamino, amidino, imino, thiocarboxylate, sulfonato, sulfamoyl, sulfonamido, nitro, trifluoromethyl, heterocyclyl, aromatic, and heteroaromatic moieties.

11. The method of any one of claims 1, 2, or 3, wherein said two-carbon spacer unit is substituted with a substituent selected from the group consisting of carboxylate, alkylcarbonyl, alkoxycarbonyl, aminocarbonyl, alkylthiocarbonyl, heterocyclyl, aromatic, and heteroaromatic moieties.

12. The method of any one of claims 1, 2, or 3, wherein said two-carbon spacer unit is substituted with a substituent selected from the group consisting of carboxylate, alkylcarbonyl, alkoxycarbonyl, aminocarbonyl, and alkyithiocarbonyl moieties.

13. The method of any one of claims 1, 2, or 3, wherein said substituted β-amino anionic compound is an α-substituted β-alanine.

14. The method of any one of claims 1, 2, or 3, wherein said substituted β-amino anionic compound is an α,α-disubstituted β-alanine.

15. The method of any one of claims 1, 2, or 3, wherein said substituted β-amino anionic compound is an α,β-disubstituted β-alanine.

16. The method of any one of claims 1, 2, or 3, wherein said substituted β-amino anionic compound is a β,β-disubstituted β-alanine.

17. The method of any one of claims 1, 2, or 3, wherein said substituted β-amino anionic compound is an α,β,α-trisubstituted β-alanine.

18. The method of any one of claims 1, 2, or 3, wherein said substituted β-amino anionic compound is an α,β,β-trisubstituted β-alanine.

19. The method of any one of claims 1, 2, or 3, wherein said substituted β-amino anionic compound is an α,α,β,β-tetrasubstituted β-alanine.

20. The method of any one of claims 1, 2, or 3, wherein said substituted β-amino anionic compound is a β-substituted β-alanine.

21. The method of any one of claims 1, 2, or 3, wherein the said β-substituted β-alanine is β-substituted with a substituent selected from the group consisting of heterocyclyl, aromatic, and heteroaromatic moieties.

22. The method of any one of claims 1, 2, or 3, wherein said substituted β-amino anionic compound is $RCH(NH_2)CH_2COOH$, wherein R is 4-fluorophenyl.

23. The method of any one of claims 1, 2, or 3, wherein said substituted β-amino anionic compound is $RCH(NH_2)CH_2COOH$, wherein R is 4-phenoxyphenyl.

24. The method of any one of claims 1, 2, or 3, wherein said substituted β-amino anionic compound is $RCH(NH_2)CH_2COOH$, wherein R is 3-(4-methylphenoxy)phenyl.

25. The method of any one of claims 1, 2, or 3, wherein said substituted β-amino anionic compound is $RCH(NH_2)CH_2COOH$, wherein R is 3-methyl-4-methoxyphenyl.

26. The method of any one of claims 1, 2, or 3, wherein said substituted β-amino anionic compound is $RCH(NH_2)CH_2COOH$, wherein R is 3-(3,4-dichlorophenoxy)phenyl.

27. The method of any one of claims 1, 2, or 3, wherein said substituted β-amino anionic compound is $RCH(NH_2)CH_2COOH$, wherein R is 2-methylphenyl.

28. The method of any one of claims 1, 2, or 3, wherein said substituted β-amino anionic compound is $RCH(NH_2)CH_2COOH$, wherein R is 3-(4-chlorophenoxy)phenyl.

29. The method of any one of claims 1, 2, or 3, wherein said substituted β-amino anionic compound is $RCH(NH_2)CH_2COOH$, wherein R is 2,5-dimethyl-4-methoxyphenyl.

30. The method of any one of claims 1, 2, or 3, wherein said substituted β-amino anionic compound is $RCH(NH_2)CH_2COOH$, wherein R is 4-trifluoromethoxyphenyl.

31. The method of any one of claims 1, 2, or 3, wherein said substituted β-amino anionic compound is $RCH(NH_2)CH_2COOH$, wherein R is 2-chlorophenyl.

32. The method of any one of claims 1, 2, or 3, wherein said substituted β-amino anionic compound is $RCH(NH_2)CH_2COOH$, wherein R is 2-fluoro-3-trifluoromethylphenyl.

33. The method of any one of claims 1, 2, or 3, wherein said substituted β-amino anionic compound is $RCH(NH_2)CH_2COOH$, wherein R is 3-bromo-4-methoxyphenyl.

34. The method of any one of claims 1, 2, or 3, wherein said substituted β-amino anionic compound is $RCH(NH_2)CH_2COOH$, wherein R is 4-bromophenyl.

35. The method of any one of claims 1, 2, or 3, wherein said substituted β-amino anionic compound is $RCH(NH_2)CH_2COOH$, wherein R is phenyl.

36. The method of any one of claims 1, 2, or 3, wherein said substituted β-amino anionic compound is $RCH(NH_2)CH_2COOH$, wherein R is 4-methylphenyl.

37. The method of any one of claims 1, 2, or 3, wherein said substituted β-amino anionic compound is $RCH(NH_2)CH_2COOH$, wherein R is 4-chlorophenyl.

38. The method of any one of claims 1, 2, or 3, wherein said substituted β-amino anionic compound is $RCH(NH_2)CH_2COOH$, wherein R is 4-acetamidophenyl.

39. The method of any one of claims 1, 2, or 3, wherein said substituted β-amino anionic compound is RCH(NH$_2$)CH$_2$COOH, wherein R is 2,5-dimethoxyphenyl.

40. The method of any one of claims 1, 2, or 3, wherein said substituted β-amino anionic compound is RCH(NH$_2$)CH$_2$COOH, wherein R is 4-diethylaminophenyl.

41. The method of any one of claims 1, 2, or 3, wherein said substituted β-amino anionic compound is RCH(NH$_2$)CH$_2$COOH, wherein R is 3-methylphenyl.

42. The method of any one of claims 1, 2, or 3, wherein said substituted β-amino anionic compound is RCH(NH$_2$)CH$_2$COOH, wherein R is 2-hydroxy-3-methoxyphenyl.

43. The method of any one of claims 1, 2, or 3, wherein said substituted β-amino anionic compound is RCH(NH$_2$)CH$_2$COOH, wherein R is 4-phenylphenyl.

44. The method of any one of claims 1, 2, or 3, wherein said substituted β-amino anionic compound is RCH(NH$_2$)CH$_2$COOH, wherein R is 3,4-dibenzyloxyphenyl.

45. The method of any one of claims 1, 2, or 3, wherein said substituted β-amino anionic compound is RCH(NH$_2$)CH$_2$COOH, wherein R is 3-[(3-trifluoromethyl)phenyloxy]phenyl.

46. The method of inhibiting epileptogenesis of claim 1, wherein $R^b$ is alkyl, alkenyl, alkynyl, cycloalkyl, aryl, alkylcarbonyl, arylcarbonyl, alkoxycarbonyl, or aryloxycarbonyl.

47. The method of inhibiting epileptogenesis of claim 1, wherein said two-carbon spacer unit is substituted with a substituent selected from the group consisting of halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, azido, heterocyclyl, aromatic, and heteroaromatic moieties.

48. The method for treating a convulsive disorder of claim 2, wherein $R^b$ is alkyl, alkenyl, alkynyl, cycloalkyl, aryl, alkylcarbonyl, arylcarbonyl, alkoxycarbonyl, or aryloxycarbonyl.

49. The method for treating a convulsive disorder of claim 2, wherein said two-carbon spacer unit is substituted with a substituent selected from the group consisting of halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, azido, heterocyclyl, aromatic, and heteroaromatic moieties.

50. The method for treating a convulsive disorder of claim 3, wherein $R^b$ is alkyl, alkenyl, alkynyl, cycloalkyl, aryl, alkylcarbonyl, arylcarbonyl, alkoxycarbonyl, or aryloxycarbonyl.

51. The method for treating a convulsive disorder of claim 3, wherein said two-carbon spacer unit is substituted with a substituent selected from the group consisting of halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, azido, heterocyclyl, aromatic, and heteroaromatic moieties.

\* \* \* \* \*

UNITED STATES PATENT AND TRADEMARK OFFICE
CERTIFICATE OF CORRECTION

PATENT NO. : 7,268,164 B2
APPLICATION NO. : 09/932677
DATED : September 11, 2007
INVENTOR(S) : Donald F. Weaver It is certified that error appears in the above-identified patent and that said Letters Patent is hereby corrected as shown below:

Claim 12, column 69 lines 52-53 states, "alkyithiocarbonyl" and should be --alkylthiocarbonyl--

Claim 31, column 70 line 46 states, "2-chiorophenyl" and should be --2-chlorophenyl--

Signed and Sealed this

Twenty-ninth Day of January, 2008

JON W. DUDAS
*Director of the United States Patent and Trademark Office*